United States Patent
Mizumoto et al.

(10) Patent No.: US 12,243,652 B2
(45) Date of Patent: Mar. 4, 2025

(54) COUNSELING METHOD AND COUNSELING DEVICE

(71) Applicant: Shiseido Company, Ltd., Tokyo (JP)

(72) Inventors: Chieko Mizumoto, Tokyo (JP); Satoshi Amano, Tokyo (JP); Seiji Satoh, Tokyo (JP); Naoto Hanyu, Tokyo (JP); Chie Yasuda, Tokyo (JP)

(73) Assignee: Shiseido Company, Ltd., Tokyo (JP)

(*) Notice: Subject to any disclaimer, the term of this patent is extended or adjusted under 35 U.S.C. 154(b) by 314 days.

(21) Appl. No.: 17/414,519

(22) PCT Filed: Dec. 19, 2019

(86) PCT No.: PCT/JP2019/049942
§ 371 (c)(1),
(2) Date: Jun. 16, 2021

(87) PCT Pub. No.: WO2020/130103
PCT Pub. Date: Jun. 25, 2020

(65) Prior Publication Data
US 2022/0051806 A1    Feb. 17, 2022

(30) Foreign Application Priority Data
Dec. 21, 2018  (JP) ................. 2018-240364

(51) Int. Cl.
*G16H 50/70* (2018.01)
*A45D 44/00* (2006.01)
(Continued)

(52) U.S. Cl.
CPC ........... *G16H 50/70* (2018.01); *A45D 44/005* (2013.01); *A61B 5/0077* (2013.01); *A61B 5/441* (2013.01);
(Continued)

(58) Field of Classification Search
CPC ........ G16H 50/70; G16H 10/40; G16H 10/60; G16H 80/00; G16H 50/30; G16H 20/10;
(Continued)

(56) References Cited

U.S. PATENT DOCUMENTS

| | | | |
|---|---|---|---|
| 2011/0301441 A1* | 12/2011 | Bandic | A61B 5/4875 600/306 |
| 2015/0045631 A1* | 2/2015 | Ademola | A61B 5/443 600/301 |
| 2016/0335910 A1* | 11/2016 | Baumann | G09B 5/00 |

FOREIGN PATENT DOCUMENTS

| | | |
|---|---|---|
| JP | 2002-056281 A | 2/2002 |
| JP | 2010-515489 A | 5/2010 |

(Continued)

OTHER PUBLICATIONS

Philips N, Auler S, Hugo R, Gonzalez S. Beneficial regulation of matrix metalloproteinases for skin health. Enzyme Res. Mar. 8, 2011;2011:427285. doi: 10.4061/2011/427285. PMID: 21423679; PMCID: PMC3057026. (Year: 2011).*

(Continued)

*Primary Examiner* — Eliza A Lam
(74) *Attorney, Agent, or Firm* — Foley & Lardner LLP

(57) ABSTRACT

Provided are a counseling method and counseling device which present a skincare advice appropriate to a user. The counseling device includes an obtaining unit that obtains genetic information representing a result of a genetic test on a user and stratum corneum information representing a result of a stratum corneum test on the user; a skin constitution determining unit that determines skin constitution of the user, based on the genetic information; a skin capability determining unit that determines skin capability representing a skin condition of the user, based on the stratum corneum information; an identifying unit that identifies a skincare advice and/or a cosmetic to be proposed to the user, (Continued)

based on the skin constitution and the skin capability; and a presenting unit that presents counseling information including information on the skincare advice and/or cosmetic to the user.

17 Claims, 14 Drawing Sheets

(51) Int. Cl.
    *A61B 5/00*           (2006.01)
    *G06Q 30/0601*     (2023.01)
    *G06Q 50/00*        (2024.01)
    *G16B 20/20*        (2019.01)
    *G16H 10/40*        (2018.01)
    *G16H 10/60*        (2018.01)
    *G16H 50/30*        (2018.01)
    *G16H 80/00*        (2018.01)

(52) U.S. Cl.
    CPC ......... *G06Q 30/0631* (2013.01); *G06Q 50/01* (2013.01); *G16B 20/20* (2019.02); *G16H 10/40* (2018.01); *G16H 10/60* (2018.01); *G16H 80/00* (2018.01); *A45D 2044/007* (2013.01); *G16H 50/30* (2018.01)

(58) Field of Classification Search
    CPC ............ A45D 44/005; A45D 2044/007; A61B 5/0077; A61B 5/441; G06Q 30/0631; G06Q 50/01; G06Q 50/10; G16B 20/20
    See application file for complete search history.

(56) References Cited

FOREIGN PATENT DOCUMENTS

| | | |
|---|---|---|
| JP | 2016-077649 A | 5/2016 |
| JP | 2016-538825 A | 12/2016 |
| JP | 2018-045539 A | 3/2018 |
| WO | WO-2008/086311 A2 | 7/2008 |
| WO | WO-2012/172625 A1 | 12/2012 |
| WO | WO-2015/048222 A1 | 4/2015 |
| WO | WO-2018/101449 A1 | 6/2018 |

OTHER PUBLICATIONS

Chika Katagiri et al. Up-regulation of serpin SCCA1 is associated with epidermal barrier disruption, Journal of Dermatological Science, vol. 57, Issue 2, (Year: 2010).*

* cited by examiner

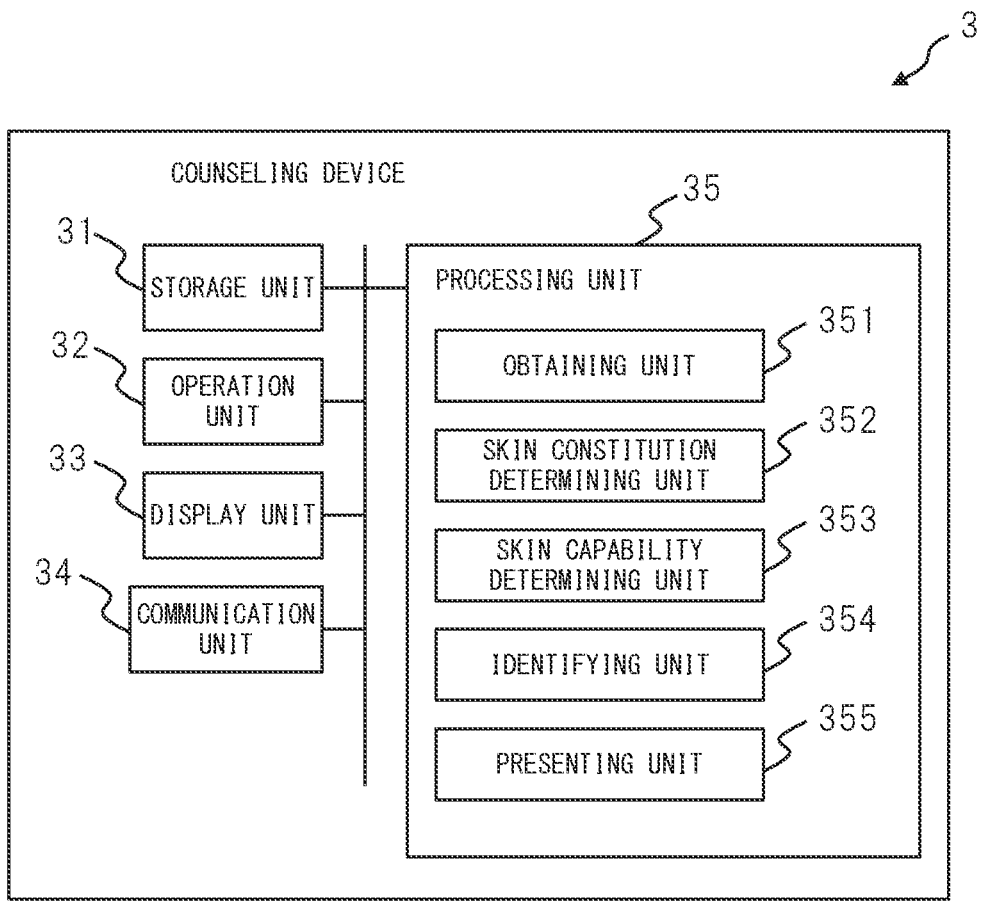

FIG. 5

| STRATUM CORNEUM COMPONENTS | MEASURED AMOUNTS | ... |
|---|---|---|
| IL-1α | 10 | ... |
| IL-1ra | 1000 | ... |
| SCCA1 | 1.0 | ... |
| MMP-9 | 40 | ... |
| ... | ... | ... |

FIG. 6

| RS NUMBERS | SKIN CHARACTERISTICS | EFFECTS | ... |
|---|---|---|---|
| rs1800629 | WRINKLES | POSITIVE | ... |
| rs1107946 | WRINKLES | NEGATIVE | ... |
| rs17822931 | BARRIER | POSITIVE | ... |
| rs1800414 | BARRIER | NEGATIVE | ... |
| ... | ... | ... | ... |

FIG. 12

| RS NUMBERS | SKIN CHARACTERISTICS | MECHANISMS | EFFECTS | ... |
|---|---|---|---|---|
| rs1800629 | WRINKLES | INFLAMMATION | POSITIVE | ... |
| rs1107946 | WRINKLES | PRODUCTION OF TYPE I COLLAGEN | NEGATIVE | ... |
| ... | ... | ... | ... | ... |

FIG. 13

| SKIN CHARACTERISTICS | MECHANISMS | RISK CRITERIA | RISK DECISIONS | ... |
|---|---|---|---|---|
| BLEMISHES | INFLAMMATION | 1, 2 | HIGH | ... |
| BLEMISHES | INFLAMMATION | 0 | MEDIUM | ... |
| BLEMISHES | INFLAMMATION | −2、−1 | LOW | ... |
| BLEMISHES | PRODUCTION OF TYPE I COLLAGEN | 2, 3 | HIGH | ... |
| ... | ... | ... | ... | ... |

FIG. 14

- 1410 — Which is your attitude to sunburn?
  - ◉ I get sunburned freely without taking precautions against UV rays.
  - ○ I take precautions against UV rays under burning sunlight.
  - ○ I try not to get sunburned in everyday life.
- 1410 — How many hours do you sleep a day on average?
  - ◉ Less than 4 hrs
  - ○ About 4 to 6 hrs
  - ○ More than 6 hrs 1400, 1420, 1430

[ SEND ]  [ CANCEL ]

FIG. 17

| IDENTIFICATION INFORMATION | CONTACT INFORMATION | GENETIC INFORMATION | | ... | GROUPS | URL |
|---|---|---|---|---|---|---|
| | | rs1800629 | rs1107946 | ... | | |
| USER 1 | abc@def.com | INCLUDED | NOT INCLUDED | ... | GROUP 1 | http://sample1.com/ |
| USER 2 | ghi@jkl.com | INCLUDED | INCLUDED | ... | GROUP 2 | http://sample2.com/ |
| ... | ... | ... | ... | ... | ... | ... |

COUNSELING METHOD AND COUNSELING DEVICE

CROSS-REFERENCE TO RELATED APPLICATIONS

This application is the U.S. National Stage of PCT/JP2019/049942, filed Dec. 19, 2019, which claims priority to JP 2018-240364, filed Dec. 21, 2018.

FIELD

The present disclosure relates to a counseling method and a counseling device.

BACKGROUND

Pharmaceuticals, cosmetics, and foods promoting users' health and beauty have been sold to respond to needs related to health and beauty. In particular, concerning health and beauty of skin, various cosmetics have been provided due to a high level of users' awareness and interest. Now users can choose cosmetics suitable for themselves from among various cosmetics, depending on their own skin constitution and current skin condition, e.g., the state of a skin barrier, moisture, pigmented spots, and wrinkles. However, to choose cosmetics suitable for themselves from among various cosmetics, users need to grasp their own skin constitution and skin condition first.

To lighten such a burden on users, a service is provided to assist a user to choose cosmetics by testing the user's own skin constitution and skin condition and presenting information on cosmetics to be recommended and advices on skin to the user, based on the result of the test. In particular, counseling is provided to present a treatment depending on the type of risk likely to arise in the user's skin, according to information on the user's genes, because it is known that there is a relation between information on a user's genes and the type of risk likely to arise in the user's skin.

For example, a device disclosed in Patent Literature 1 obtains gene polymorphism information on a user's genes, determines the presence or absence of genetic characteristics related to the user's own skin constitution, based on the obtained gene polymorphism information, and presents a treatment depending on the genetic characteristics.

CITATION LIST

Patent Literature

Patent Literature 1: Japanese Unexamined Patent Publication No. 2018-45539

SUMMARY

However, it is known that the skin condition is subjected to both effects of a user's past and current living environment and lifestyle (hereafter, "external and internal risk"), such as daily skin damage caused by ultraviolet rays and the state of skincare, and genetic characteristics based on genetic information. Thus, to present information on an appropriate skincare advice and cosmetic to a user, it is necessary, in counseling, to take account of external and internal risk factors obtained by testing both the skin condition and skin genetic characteristics.

An object of the counseling method and the counseling device is to present a skincare advice appropriate to a user.

A counseling method according to an embodiment includes obtaining genetic information representing a result of a genetic test on a user and stratum corneum information representing a result of a stratum corneum test on the user; determining skin constitution of the user, based on the genetic information; determining skin capability of the user, based on the stratum corneum information; identifying a skincare advice and/or a cosmetic to be proposed to the user, based on the skin constitution and the skin capability; and presenting counseling information including information on the skincare advice and/or cosmetic to the user, based on the identified skin constitution and skin capability.

In the present disclosure, skincare advices include an advice related to anything that contributes to keep skin healthy and beautiful, such as lifestyle including sleep and physical exercise; ingredients for skincare suitable for a user; and skincare techniques and diets suitable for a user, including cosmetics, dietary supplements, and beautification appliances. The information on a skincare advice and/or a cosmetic may include recommendatory information on a product.

In the counseling method according to the embodiment, the counseling information preferably includes information on the skin constitution and information on the skin capability.

The counseling method according to the embodiment preferably includes obtaining attribute information or preference information of the user, and identifying the skincare advice and/or cosmetic is preferably further based on the attribute information or preference information.

In the counseling method according to the embodiment, the stratum corneum information preferably includes results of stratum corneum tests obtained at different times, and determining the skin capability preferably includes determining a changing pattern of skin capability on the basis of the stratum corneum information.

The counseling method according to the embodiment preferably includes obtaining skin image information based on a skin image of the user's skin, and identifying the skincare advice and/or cosmetic is preferably further based on the skin image information.

The counseling method according to the embodiment preferably includes obtaining attribute information or preference information of the user and skin image information based on a skin image of the user's skin, and identifying the skincare advice preferably includes extracting a factor affecting the user's skin, based on the skin capability, the attribute information or preference information, and the skin image information, and identifying the skincare advice, based on the skin constitution and the extracted factor.

In the counseling method according to the embodiment, the counseling information preferably includes information on a community for a user to exchange information with another user or to obtain information on a skincare advice and/or a cosmetic.

In the counseling method according to the embodiment, the counseling information preferably includes information on skin stability.

A counseling device according to an embodiment includes an obtaining unit that obtains genetic information representing a result of a genetic test on a user and stratum corneum information representing a result of a stratum corneum test on the user; a skin constitution determining unit that determines skin constitution of the user, based on the genetic information; a skin capability determining unit that determines skin capability representing a skin condition of the user, based on the stratum corneum information; an identifying unit that identifies a skincare advice and/or a cosmetic to be proposed to the user, based on the skin constitution and the skin capability; and a presenting unit that presents counseling information including information on the skincare advice and/or cosmetic to the user.

According to the embodiment, the counseling method and the counseling device enable presenting a skincare advice more appropriate to the user.

The objects and advantageous effects of the present invention will be understood and achieved by means of constituent features and combinations thereof mentioned, in particular, in the claims. Both the above general and the following detailed descriptions are illustrative and explanatory ones, and do not limit the claimed invention.

BRIEF DESCRIPTION OF DRAWINGS

FIG. 3 shows an example of a schematic configuration of the counseling device 3.

FIG. 4 shows an example of the data structure of genetic information.

FIG. 5 shows an example of the data structure of stratum corneum information.

FIG. 6 shows an example of the data structure of an SNP table 600.

FIG. 12 shows an example of the data structure of an SNP table 600a.

FIG. 13 shows an example of the data structure of a table 700a for determining genetic characteristics.

FIG. 14 shows an example of a questionnaire information input screen 1400.

FIG. 15 shows an example of the data structure of a skincare advice table 900a.

FIG. 17 shows an example of the data structure of a user information table 1700.

FIG. 18 shows an example of a counseling information display image 1000a.

DESCRIPTION OF EMBODIMENTS

Hereinafter, various embodiments of the present invention will be described with reference to the drawings. However, note that the technical scope of the present invention is not limited to these embodiments and includes the invention described in the claims and equivalents thereof.

Figure 1:
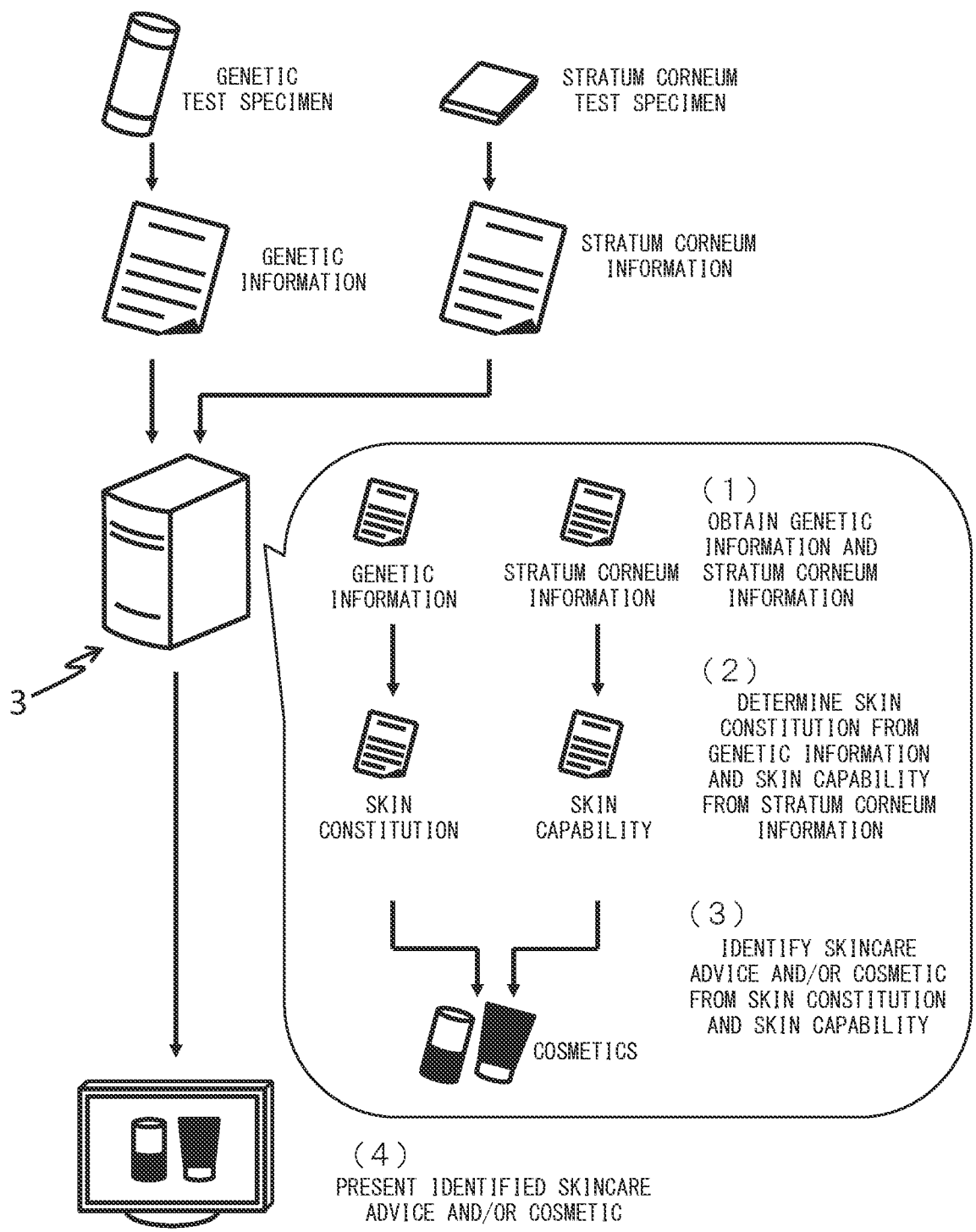
FIG. 1 schematically shows an example of processing by a counseling device 3.

FIG. 1 schematically shows an example of processing by a counseling device 3.

The counseling device 3 identifies a skincare advice and a cosmetic suitable for a user, based on genetic information representing the result of a genetic test on a user and stratum corneum information representing the result of a stratum corneum test on the user, and presents information on the identified skincare advice and cosmetic to the user. The counseling device 3 is, for example, a personal computer (PC) placed in a store run by a provider of a service. The counseling device 3 may be a multifunctional mobile phone ("smartphone") managed by a salesclerk of the store or a server placed outside the store.

As shown in FIG. 1 (1), the counseling device 3 obtains genetic information and stratum corneum information of a user. The genetic information is information representing the result of a genetic test. The genetic information is, for example, information indicating whether a certain gene of the user includes a variation of a certain single nucleotide polymorphism (SNP) known to be related to particular properties or conditions of skin (skin characteristics). The skin characteristics are properties or conditions, such as a skin barrier, moisture, pigmented spots, wrinkles, skin unstableness, sunburn damage, skin sensitivity, and skin roughness. An SNP refers to a mutation of some of bases in a base sequence of a particular species (e.g., the yellow race) known to appear in this particular species with a frequency not less than a certain frequency (e.g., 1 percent). It is known to be related to particular skin characteristics, e.g., those who have a certain SNP are more likely or unlikely to have skin pigmented spots than those who do not have this SNP. The stratum corneum information is information representing the result of a stratum corneum test. The stratum corneum information is, for example, information on the content and biochemical or morphological characteristics of a certain stratum corneum component obtained by various tests on stratum corneum of the user's skin and known to be related to skin characteristics.

In the following, of variations of an SNP known to be related to skin characteristics, a variation affecting a user's skin characteristics will be simply referred to as an "SNP" in some cases.

Then, as shown in FIG. 1 (2), the counseling device 3 determines skin constitution of the user, based on the genetic information. The skin constitution is information representing the constitution of the user's skin. The skin constitution is information representing genetic characteristics of the user's skin for each skin characteristic. The skin constitution is information indicating a skin characteristic that may become a problem in the user's skin in the future.

Additionally, the counseling device 3 determines skin capability of the user, based on the stratum corneum information. The skin capability is information indicating how much external and internal stimuli affect the user's skin and become risks for each skin characteristic. The skin capability may be information representing capability of the user's skin to become beautiful. The skin capability is information indicating a skin characteristic that is a problem or may become a problem in the near future in the user's skin.

Then, as shown in FIG. 1 (3), the counseling device 3 identifies a skincare advice and a cosmetic to be proposed to the user, based on the skin constitution and the skin capability. Then, as shown in FIG. 1 (4), the counseling device 3 presents counseling information including information on the identified skincare advice and cosmetic to the user, and terminates a series of steps of processing.

In this way, the counseling device 3 obtains genetic information representing the result of a genetic test on a user and stratum corneum information representing the result of a stratum corneum test on the user; determines skin constitution of the user, based on the genetic information; determines skin capability of the user, based on the stratum corneum information; identifies a skincare advice and/or a cosmetic to be proposed to the user, based on the skin constitution and the skin capability; and presents counseling information including information on the skincare advice and/or cosmetic to the user. This enables the counseling device 3 to present information on a skincare advice and a cosmetic more appropriate to the user, based on genetic characteristics represented by skin constitution information and external and internal risk represented by skin capability information.

Figure 2:
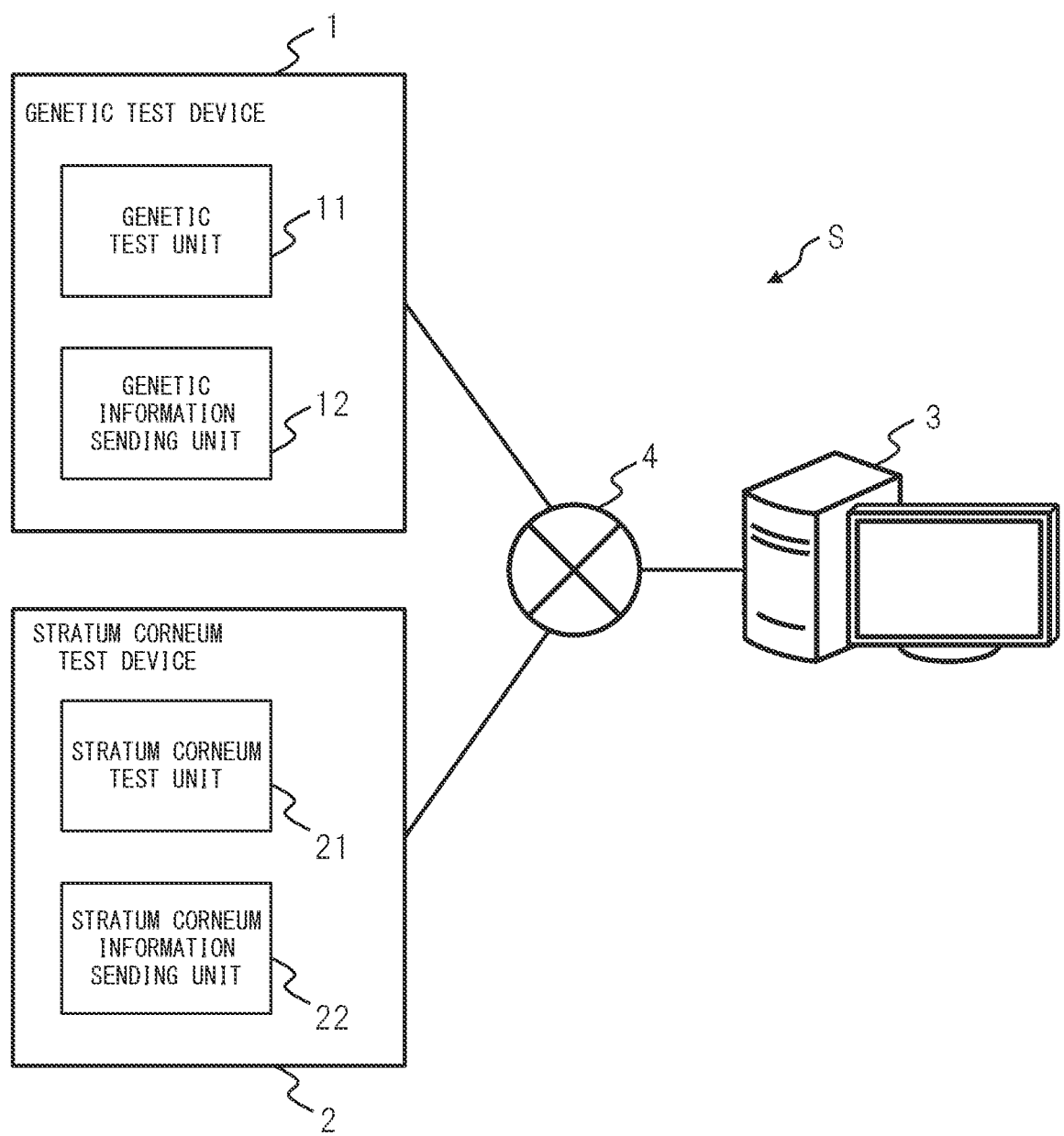
FIG. 2 shows an example of a schematic configuration of a counseling system S.

FIG. 2 shows an example of a schematic configuration of a counseling system S. The counseling system S includes a genetic test device 1, a stratum corneum test device 2, and the counseling device 3. In the counseling system S, the genetic test device 1, the stratum corneum test device 2, and the counseling device 3 are connected via a network 4, such as the Internet or an intranet, so that they can communicate with each other.

The genetic test device 1 performs a genetic test on a genetic test specimen obtained from a user's body, generates genetic information representing the result of the genetic test, and sends the generated genetic information to the counseling device 3. To this end, the genetic test device 1 includes a genetic test unit 11 and a genetic information sending unit 12.

The genetic test unit 11 performs a genetic test on a genetic test specimen, and generates genetic information. The genetic information is, for example, information indicating whether a user's genes have a certain mutation type of SNP.

The genetic test unit 11 generates genetic information from a genetic test specimen. The genetic test specimen is, for example, a user's saliva, blood, or mucosa, but is not limited thereto as long as it is a specimen from which a nucleic acid of the user can be purified. The following describes an example of a genetic information generating process for the genetic test unit 11 to generate genetic information from a genetic test specimen. First, the genetic test unit 11 purifies a nucleic acid of a user from a specimen, using a known technique. Then, the genetic test unit 11 tries to detect a certain mutation type of a SNP in the generated nucleic acid, which is a deoxyribonucleic acid (DNA), thereby determining the presence or absence of the certain mutation type of the SNP. The certain SNP is an SNP known to be related to a skin characteristic. As the certain SNP, single or multiple SNPs may be appropriately selected for each skin characteristic. The certain SNP is detected, for example, by a method using a polymerase chain reaction (PCR) or a DNA probe. Then, the genetic test unit 11 records the presence or absence of the certain mutation type of the SNP as computer-readable digital data to generate genetic information.

The genetic test unit 11 is, for example, a commercially available genetic test device that can perform the above genetic information generating process. The genetic test unit 11 may be a combination of a nucleic acid purifying device that can purify a nucleic acid as above and an SNP detecting device that can detect an SNP. Part or all of the genetic information generating process may be performed by a tester.

The genetic information sending unit 12 sends the generated genetic information to the counseling device 3. To this end, the genetic information sending unit 12 includes a communication interface circuit for communicating with the counseling device 3 via the network 4. The communication interface circuit included in the genetic information sending unit 12 is, for example, a communication interface circuit of a wired local area network (LAN). The genetic information sending unit 12 sends the generated genetic information to the counseling device 3 via the network 4 automatically or in response to a request from an operator of the genetic test device 1 or from the counseling device 3.

The genetic information sending unit 12 may provide the genetic information for the counseling device 3 without passing through the network 4. For example, the genetic information sending unit 12 may output the genetic information to an external storage medium, such as a compact disc read-only memory (CD-ROM), via an output unit (not shown), and make the counseling device 3 read the external storage medium to provide the genetic information. In this case, part or all of the process to output the genetic information to an external storage medium and to make the counseling device 3 read the external storage medium may be performed by a tester.

The stratum corneum test device 2 performs a stratum corneum test on a stratum corneum sample obtained from a user's body with, for example, an adhesive tape, generates stratum corneum information representing the result of the stratum corneum test, and sends the generated stratum corneum information to the counseling device 3. To this end, the stratum corneum test device 2 includes a stratum corneum test unit 21 and a stratum corneum information sending unit 22.

The stratum corneum test unit 21 performs a stratum corneum test on a stratum corneum sample, and generates stratum corneum information. The stratum corneum information is information on the content and biochemical or morphological characteristics of a certain stratum corneum component known to be related to a skin characteristic.

The stratum corneum test unit 21 generates stratum corneum information from a stratum corneum sample. The stratum corneum sample is, for example, tissue of the surface of a user's skin taken with an adhesive tape, but is not limited thereto as long as it includes stratum corneum cells. The following describes a stratum corneum information generating process for the stratum corneum test unit 21 to generate stratum corneum information from a stratum corneum test specimen. The stratum corneum test unit 21 measures the content and biochemical or morphological characteristics of a certain stratum corneum component. For example, the stratum corneum test unit 21 measures the amount of stratum-corneum inflammatory protein known to correlate with a skin barrier and skin sensitivity. The amount of stratum-corneum inflammatory protein can be measured through a stratum corneum test on a stratum corneum sample, using a technique such as enzyme-linked immunosorbent assay (ELISA). Then, the stratum corneum test unit 21 records information on the measured content and biochemical or morphological characteristics of the stratum corneum component as computer-readable digital data to generate stratum corneum information.

The stratum corneum test unit 21 is, for example, a commercially available stratum corneum test device that can perform the stratum corneum information generating process. The stratum corneum test unit 21 may be a combination of stratum corneum test devices that can perform different stratum corneum information generating processes, respectively. Part or all of the stratum corneum information generating process may be performed by a tester.

The stratum corneum information sending unit 22 sends the generated stratum corneum information to the counseling device 3. To this end, the stratum corneum information sending unit 22 includes, for example, a communication interface circuit of a wired LAN for communicating with the counseling device 3 via the network 4. The stratum corneum information sending unit 22 sends the generated stratum corneum information to the counseling device 3 via the network 4 automatically or in response to a request from an operator of the stratum corneum test device 2 or from the counseling device 3. The stratum corneum information sending unit 22 may provide the stratum corneum information for the counseling device 3 without passing through the network 4, as described above.

FIG. 3 shows an example of a schematic configuration of the counseling device 3. The counseling device 3 includes a storage unit 31, an operation unit 32, a display unit 33, a communication unit 34, and a processing unit 35.

The storage unit 31 is a device storing programs or data, and includes, for example, a semiconductor memory device. The storage unit 31 stores data and programs used for processing by the processing unit 35, such as an operating system program, a device driver program, and an application program. The programs are installed on the storage unit 31, for example, from a computer-readable and portable storage medium, such as a CD-ROM or a digital versatile disc read-only memory (DVD-ROM), using a known set-up program.

The operation unit 32 is a device enabling operation of the counseling device 3, e.g., a touch screen, a keyboard, or a mouse. An operator of the counseling device 3 can input, for example, letters, numerals, and symbols with the operation unit 32. When operated by an operator, the operation unit 32 generates an operation signal corresponding to the operation. The operation unit 32 supplies the generated signal to the processing unit 35.

The display unit 33 is a device for displaying moving or still images, e.g., a liquid crystal display or an organic electroluminescent display. The display unit 33 may be integrated with the operation unit 32 that is a touch screen. The display unit 33 displays moving or still images according to video data and image data supplied from the processing unit 35.

The communication unit 34 includes a communication interface circuit for the counseling device 3 to communicate with another device, such as the genetic test device 1 and the stratum corneum test device 2, via the network 4. The communication interface circuit included in the communication unit 34 is a communication interface circuit of a wired LAN. The communication interface circuit included in the communication unit 34 may be, for example, a communication interface circuit of long term evolution (LTE) or a wireless LAN. The communication unit 34 supplies data received from another device, such as the genetic test device 1 and the stratum corneum test device 2, to the processing unit 35.

The processing unit 35 includes one or more processors and a peripheral circuit thereof. The processing unit 35 is, for example, a central processing unit (CPU), and centrally controls the entire operation of the counseling device 3. The processing unit 35 may be a digital signal processor (DSP), a large-scale integrated circuit (LSI), an application specific integrated circuit (ASIC), or a field programmable gate array (FPGA). The processing unit 35 controls the operation of the display unit 33 and the communication unit 34 so that various processes of the counseling device 3 may be executed by an appropriate procedure, based on the programs stored in the storage unit 31 and operation signals supplied from the operation unit 32. The processing unit 35 executes processing, based on the programs stored in the storage unit 31. The processing unit 35 can execute multiple programs in parallel.

The processing unit 35 includes an obtaining unit 351, a skin constitution determining unit 352, a skin capability determining unit 353, an identifying unit 354, and a presenting unit 355. These units are functional modules implemented by a program executed on the processor included in the processing unit 35. Alternatively, these units may be implemented in the counseling device 3 as firmware.

The obtaining unit 351 obtains genetic information representing the result of a genetic test on a user and stratum corneum information representing the result of a stratum corneum test on the user. For example, the obtaining unit 351 controls the communication unit 34 to receive genetic information from the genetic test device 1 as digital data, thereby obtaining the genetic information. The obtaining unit 351 also controls the communication unit 34 to receive stratum corneum information from the stratum corneum test device 2 as digital data, thereby obtaining the stratum corneum information. The obtaining unit 351 may obtain the genetic information and the stratum corneum information by another method. For example, it may control the communication unit 34 to receive genetic information or stratum corneum information that has already obtained from a previous test from another terminal (not shown) as digital data. The obtaining unit 351 may generate genetic information or stratum corneum information in response to a tester operating the operation unit 32, thereby obtaining the genetic information or the stratum corneum information.

FIG. 4 shows an example of the data structure of genetic information 400. In the genetic information 400, gene names 410, ID numbers 420 of reference SNPs (RS numbers), mutations 430, measurement results 440, and other data are stored in association with each other. In the gene names 410, the names of genes including certain SNPs known to be related to skin characteristics are stored. In the RS numbers 420, RS numbers by which the certain SNPs are uniquely identifiable are stored. The RS numbers are numbers by which the SNPs are uniquely identifiable. Detailed information, such as the names of genes including the SNPs corresponding to the RS numbers and sequence information representing the base sequences of the SNPs, is disclosed, for example, on the website of the National Center for Biotechnology Information (NCBI) of the United States. In the mutations 430, information representing details of mutations in the base sequences of the associated SNPs is stored. In the measurement results 440, information indicating whether mutations in the associated SNPs are included in the user's genes is stored.

The example of FIG. 4 illustrates that the SNP included in gene "TNF" and corresponding to RS number "rs1800629" has a base "G (guanine)" in the gene at the position of "31575254" substituted with "A (adenine)," and that the mutation type of the SNP corresponding to RS number "rs1800629" is detected from the user's gene as the result of a test by the genetic test device 1. The example of FIG. 4 also illustrates that the SNP included in gene "ABCC11" and corresponding to RS number "rs17822931" has a base "C (cytosine)" in the gene at the position of "48224287" substituted with "T (thymine)," and that the mutation type of the SNP corresponding to RS number "rs17822931" is not detected from the user's gene as the result of a test by the genetic test device 1.

FIG. 5 shows an example of the data structure of stratum corneum information 500. In the stratum corneum information 500, stratum corneum components 510, measured amounts 520, and other data are stored in association with each other. In the stratum corneum components 510, names or other information by which certain stratum corneum components, such as protein, known to correlate with skin characteristics are identifiable are stored. In the measured amounts 520, measured amounts obtained by stratum corneum tests and representing the content and biochemical or morphological characteristics of the associated stratum corneum components are stored.

With reference to FIG. 3 again, the skin constitution determining unit 352 determines skin constitution of the user, based on the genetic information. The skin constitution is information representing genetic characteristics of the user's skin for each skin characteristic.

For example, the skin constitution determining unit 352 refers to an SNP table 600 stored in the storage unit 31 to compute an SNP score for each skin characteristic, based on the genetic information obtained by the obtaining unit 351.

FIG. 6 shows an example of the data structure of the SNP table 600. The SNP table 600 stores RS numbers 610, skin characteristics 620, effects 630, and other data in association with each other. In the skin characteristics 620, information for identifying items of skin characteristics is stored. For example, in each skin characteristic 620, one of the names of items of certain skin characteristics, such as skin "barrier," "moisture," "pigmented spots," "wrinkles," "sunburn damage," "sensitivity," "skin roughness," and "skin unstableness," are stored. In the skin characteristics 620, identification information for identifying items of the certain skin characteristics may be stored.

The barrier shows whether the amount of transepidermal water loss from skin is large or small. A large amount of transepidermal water loss indicates a strong skin barrier, and a small amount of transepidermal water loss indicates a weak skin barrier. The moisture shows whether the moisture content in stratum corneum is high or low. A high moisture content indicates moist skin, and a low moisture content indicates dry skin. The pigmented spots show the number of color irregularities appearing when the degree of pigmentation in an area of skin caused by an increase in generation of melanin differs from that of pigmentation in a surrounding area. A large number of color irregularities of pigmentation indicate many skin pigmented spots, and a small number of color irregularities of pigmentation indicate few skin pigmented spots. The wrinkles are deformation of epidermis or dermis of skin. A high degree of deformation indicates deep skin wrinkles, and a low degree of deformation indicates narrow skin wrinkles. The sunburn damage is damage to skin suffered by exposure to sunlight, and shows a change in skin that has not lead to pigmented spots, wrinkles, nor sunburn. The higher the degree of changes in appearance of protein caused by sunburn, the higher the estimation of sunburn damage. The sensitivity shows the degree of susceptibility to a skin trouble caused by an external or internal stimulus. The higher the degree of susceptibility to a skin trouble, the higher the estimation of sensitivity. The skin roughness shows the degree of changes in skin, such as dryness, stiffness, and redness of skin. The higher the degree of changes in skin, the higher the estimation of skin roughness. The skin unstableness shows intermittent skin deterioration that does not result from particular stimuli. The higher the frequency or degree of skin deterioration, the higher the estimation of skin unstableness.

The items of skin characteristics are not limited to the above ones, and other items may be provided. For example, items of skin characteristics of each body part, such as barriers of cheeks and arms, may be provided. Items of skin characteristics fractionized according to evaluation methods, such as the number of pigmented spots and the average area of pigmented spots, may be provided. Items of skin characteristics fractionized according to variable factors of skin characteristics, such as furrows and fine lines, may be provided. Other items of skin characteristics, such as skin texture and skin firmness, may be provided.

In the effects 630, information for identifying how the SNPs corresponding to the associated RS numbers affect the associated skin characteristics is stored. For example, in the effects 630, "positive" or "negative" is stored. Effect "positive" means that the associated skin characteristic is more likely to appear in a user having the associated mutation type at SNP. Effect "negative" means that the associated skin characteristic is less likely to appear in a user having mutation type at the associated SNP.

In the example shown in FIG. 6, a mutation type at RS number "rs1800629" is stored in association with skin characteristic "wrinkles" and effect "positive." Hence the mutation type at SNP corresponding to RS number "rs1800629" has a positive effect on skin characteristic "wrinkles." Thus, the SNP table 600 stores information indicating that a user having the mutation type at SNP corresponding to RS number "rs1800629" has a genetic predisposition to have more skin wrinkles than a user who does not have this SNP. RS number "rs1800414" is stored in association with skin characteristic "barrier" and effect "negative." Thus, the SNP table 600 stores information indicating that a user having the mutation type at SNP corresponding to RS number "rs1800414" has a genetic predisposition to have a weaker skin barrier than a user who does not have this mutation type at SNP.

In the example shown in FIG. 6, each skin characteristic is associated with multiple SNPs, but the SNP table 600 may store a single SNP for each skin characteristic in association therewith.

With reference to FIG. 3 again, the skin constitution determining unit 352 selects a skin characteristic to compute an SNP score of. The skin constitution determining unit 352 refers to the SNP table 600, and obtains RS numbers associated with the selected skin characteristic and with effect "positive" of the RS numbers corresponding to the SNPs included in the user's genes. The skin constitution determining unit 352 also obtains RS numbers associated with the selected skin characteristic and with effect "negative" of the RS numbers corresponding to the SNPs included in the user's genes. The skin constitution determining unit 352 computes a skin constitution score depending on the presence or absence of mutation type at the SNPs associated with the obtained RS numbers, based on a constitution evaluating algorithm depending on the skin constitution.

The skin constitution determining unit 352 executes the above procedure for each skin characteristic to compute a skin constitution score for each skin characteristic.

The following describes an example of the procedure by which the skin constitution determining unit 352 computes a skin constitution score by referring to the SNP table 600 shown in FIG. 6, using an example of the genetic information 400 shown in FIG. 4. First, the skin constitution determining unit 352 selects skin characteristic "wrinkles" to compute a skin constitution score of. Then, of the RS numbers corresponding to the SNPs included in the user's genes, the skin constitution determining unit 352 counts the number of mutation types at RS numbers associated with skin characteristic "wrinkles" and with effect "positive," and makes this number be the score value of effect "positive." In FIG. 4, since the user's genes include the mutation type at SNP corresponding to RS number "rs1800629" associated with skin characteristic "wrinkles" and with effect "positive," the number of mutation types at RS numbers is counted as "1" and the score value of effect "positive" is "1." Then, of the mutation types at RS numbers corresponding to the SNPs included in the user's genes, the skin constitution determining unit 352 counts the number of mutation types at RS numbers associated with skin characteristic "wrinkles" and with effect "negative," and makes this number be the score value of effect "negative." In FIG. 4, since the user's genes do not include the mutation type at SNP corresponding to RS number "rs1107946" associated with skin characteristic "wrinkles" and with effect "negative," the number of RS numbers is counted as "0" and the score value of effect "negative" is "0." Then, the skin constitution determining unit 352 subtracts the score value, "0," of effect "negative" from the score value, "1," of effect "positive" to compute a skin constitution score of skin characteristic "wrinkles" as "1."

The skin constitution score may be computed as follows. First, the skin constitution determining unit 352 selects skin characteristic "wrinkles" to compute a skin constitution score of. Then, the skin constitution determining unit 352 identifies the RS numbers associated with skin characteristic "wrinkles," and generates variables respectively corresponding to the identified RS numbers. Then, the skin constitution determining unit 352 sets the variables corresponding to the identified RS numbers to "0," if the mutation type at SNPs corresponding to these RS numbers are not included in the user's genes, and to "1," if the mutation type at SNPs corresponding to these RS numbers are included in the user's genes. Then, the skin constitution determining unit 352 computes a skin constitution score of skin characteristic "wrinkles" in accordance with a specific algorithm, based on the variables corresponding to the identified RS numbers. The specific algorithm is, for example, an algorithm including assigning certain weights to the variables corresponding to the mutation types at RS numbers associated with skin characteristic "wrinkles," depending on how much the mutation types at SNPs corresponding to the RS numbers affect skin characteristic "wrinkles," and computing the sum total thereof. The specific algorithm may be an algorithm to compute a skin constitution score by other computations based on the variables corresponding to the mutation types at RS numbers associated with skin characteristic "wrinkles." The specific algorithm may be an algorithm to determine a skin constitution score, by referring to a table or other data prestored in the storage unit 31, based on a combination of values set to the variables corresponding to the mutation type at RS numbers associated with skin characteristic "wrinkles." The specific algorithm may be different for each skin characteristic.

The skin constitution determining unit 352 executes the above procedure regarding skin characteristic "barrier" to compute a skin constitution score of skin characteristic "barrier." In this way, the skin constitution determining unit 352 computes a skin constitution score for each skin characteristic.

The skin constitution determining unit 352 refers to a table 700 for determining genetic characteristics stored in the storage unit 31 to determine genetic characteristics for each skin characteristic, based on the skin constitution scores computed for each skin characteristic.

Figure 7:
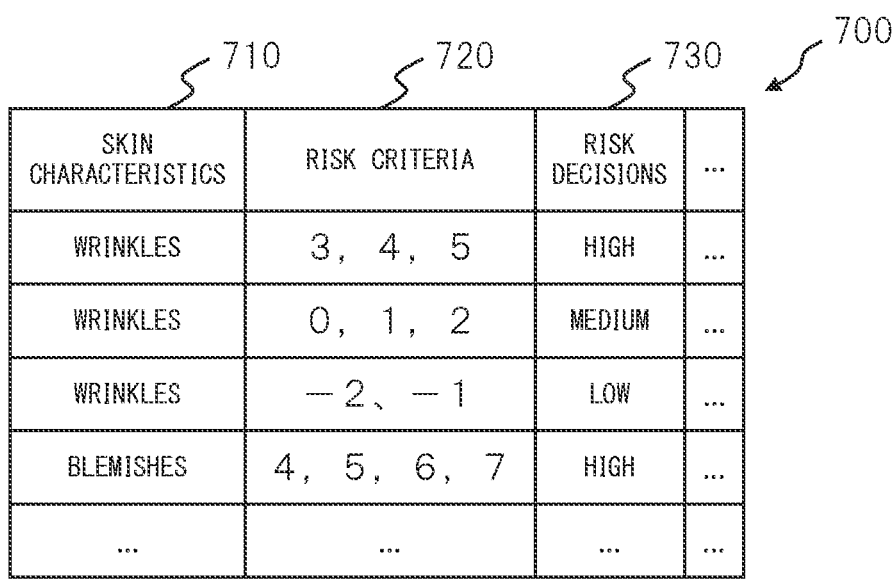
FIG. 7 shows an example of the data structure of a table 700 for determining genetic characteristics.

FIG. 7 shows an example of the data structure of the table 700 for determining genetic characteristics. The table 700 stores skin characteristics 710, risk criteria 720, risk decisions 730, and other data in association with each other. In the risk criteria 720, conditions related to skin constitution scores of skin characteristics associated therewith are stored. In the risk decisions 730, information representing the degrees of risk based on genetic characteristics for the case that the associated risk criteria are satisfied is stored.

In the example shown in FIG. 7, if the skin constitution score of skin wrinkles is "3, 4, or 5," it is determined that risk based on genetic characteristics related to skin wrinkles is high. If the skin constitution score of skin wrinkles is "0, 1, or 2," it is determined that risk based on genetic characteristics related to skin wrinkles is medium. If the skin constitution score of skin wrinkles is "−2 or −1," it is determined that risk based on genetic characteristics related to skin wrinkles is low.

For example, if the number of mutation types at SNPs having a positive effect on skin wrinkles is five and that of mutation types at SNPs having a negative effect thereon is two in the SNP table 600, the range of a computed skin constitution score of skin wrinkles is not less than "−2" nor greater than "5." If the user's genetic information includes all of these SNPs, the skin constitution score of skin wrinkles is 3. In the example shown in FIG. 7, the risk criteria 720 are defined so that a skin constitution score "3, 4, or 5" of skin wrinkles leads to the determination that risk based on genetic characteristics related to skin wrinkles is high. The risk criteria 720 are also defined so that a skin constitution score "0, 1, or 2" of skin wrinkles leads to the determination that risk based on genetic characteristics related to skin wrinkles is medium. The risk criteria 720 are also defined so that a skin constitution score "−2 or −1" of skin wrinkles leads to the determination that risk based on genetic characteristics related to skin wrinkles is low.

The risk criteria 720 may be defined differently for each skin characteristic. For example, the risk criteria 720 may be defined differently for each skin characteristic, depending on the number of mutation types at SNPs having a positive effect on skin characteristics and that of mutation types at SNPs having a negative effect thereon.

With reference to FIG. 3 again, the skin constitution determining unit 352 selects a skin characteristic regarding which genetic characteristics will be determined. Then, the skin constitution determining unit 352 refers to the table 700 for determining genetic characteristics and compares the risk criteria associated with the selected skin characteristic with the skin constitution score of the selected skin characteristic to determine genetic characteristics regarding the selected skin characteristic.

The skin constitution determining unit 352 executes the above procedure for each skin characteristic to determine genetic characteristics for each skin characteristic. In this way, the skin constitution determining unit 352 determines skin constitution of the user.

The skin capability determining unit 353 determines skin capability of the user, based on the stratum corneum information. The skin capability is information indicating how much external and internal risk factors affect the user's skin for each skin characteristic.

For example, the skin capability determining unit 353 refers to a table 800 for determining external and internal risk stored in the storage unit 31 to determine the degree of external and internal risk for each skin characteristic, based on the stratum corneum information obtained by the obtaining unit 351.

Figure 8:
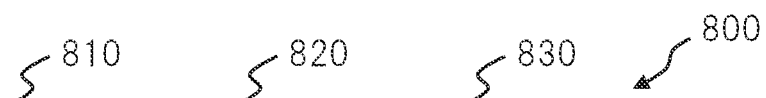
FIG. 8 shows an example of the data structure of a table 800 for determining external and internal risk.

FIG. 8 shows an example of the data structure of the table 800 for determining external and internal risk. The table 800 stores skin characteristics 810, risk criteria 820, risk decisions 830, and other data in association with each other. In the risk criteria 820, information for identifying stratum corneum components and conditions related to measured amounts of stratum corneum components are stored in association with each other. In the risk decisions 830, information for identifying the degrees of external and internal risk for the case that the associated risk criteria are satisfied is stored.

In the example shown in FIG. 8, if the measured amount of stratum corneum component "SCCA-1" is "not less than 3.0," it is determined that risk related to the skin barrier is high. If the measured amount of stratum corneum component "SCCA-1" is "not less than 1.0 and less than 3.0," it is determined that risk related to the skin barrier is medium. If the measured amount of stratum corneum component "SCCA-1" is "less than 1.0," it is determined that risk related to the skin barrier is low. If the measured amount of stratum corneum component "MMP-9" is "not less than 40," it is determined that risk related to sunburn damage of skin is high.

In each risk criterion 820, information for identifying multiple stratum corneum components and conditions related to the relationship between measured amounts of multiple stratum corneum components may be stored in association with each other. In the example shown in FIG. 8, if the value of "IL-1ra/IL-1α" is "not less than 100," it is determined that risk related to sensitive skin is high. The value of "IL-1ra/IL-1α" refers to a value indicating the ratio of a measured amount of stratum corneum component "IL-1ra" to a measured amount of stratum corneum component "IL-1α." The conditions related to the relationship between measured amounts of multiple stratum corneum components are not limited to conditions related to ratios, and may be any conditions, such as conditions related to a sum of measured amounts of multiple stratum corneum components and a magnitude relationship therebetween. Additionally, in the example shown in FIG. 8, the risk criteria 820 are defined based on stratum corneum components differing among the skin characteristics 810, but the risk criteria 820 of multiple skin characteristics may be defined based on the same stratum corneum component. In this case, the risk criteria 820 may be defined independently for each skin characteristic 810. For example, the risk criteria 820 may be defined so that the value of "IL-1ra/IL-1α" not less than "100" leads to the determination that risk related to sensitive skin is high, and the value not less than "10" leads to the determination that risk related to the skin barrier is high.

With reference to FIG. 3 again, the skin capability determining unit 353 selects a skin characteristic regarding which the degree of external and internal risk will be determined. Then, the skin capability determining unit 353 refers to the table 800 for determining external and internal risk and compares the risk criteria associated with the selected skin characteristic with the types and measured amounts of the stratum corneum components included in stratum corneum information to determine the degree of external and internal risk regarding the selected skin characteristic.

The skin capability determining unit 353 executes the above procedure for each skin characteristic to determine the degree of external and internal risk for each skin characteristic. In this way, the skin capability determining unit 353 determines skin capability of the user.

The identifying unit 354 identifies a skincare advice and a cosmetic to be proposed to the user, based on the skin constitution and the skin capability. For example, the identifying unit 354 selects a skin characteristic regarding which it is determined by the skin constitution determining unit 352 that genetic risk is high and determined by the skin capability determining unit 353 that external and internal risk is high. The identifying unit 354 refers to a skincare advice table 900 and a cosmetic table 910 stored in the storage unit 31 to identify a skincare advice and a cosmetic corresponding to the selected skin characteristic as a skincare advice and a cosmetic to be proposed to the user.

If there are multiple skin characteristics regarding which both the risk based on genetic characteristics and the external and internal risk are high, the identifying unit 354 may select these skin characteristics or some of them in preset priority order. The preset priority order may be common to users or set on a user-by-user basis, based on the results of questionnaires to the users. If there is a skin characteristic regarding which only the risk based on genetic characteristics or the external and internal risk is high, the identifying unit 354 may select the skin characteristic regarding which the risk based on genetic characteristics or the external and internal risk is high. If there is no skin characteristic regarding which the risk based on genetic characteristics or the external and internal risk is high, the identifying unit 354 may select a skin characteristic regarding which both the risk based on genetic characteristics and the external and internal risk are medium. Alternatively, the identifying unit 354 may identify a preset skincare advice and cosmetic without selecting a skin characteristic.

Figure 9A:
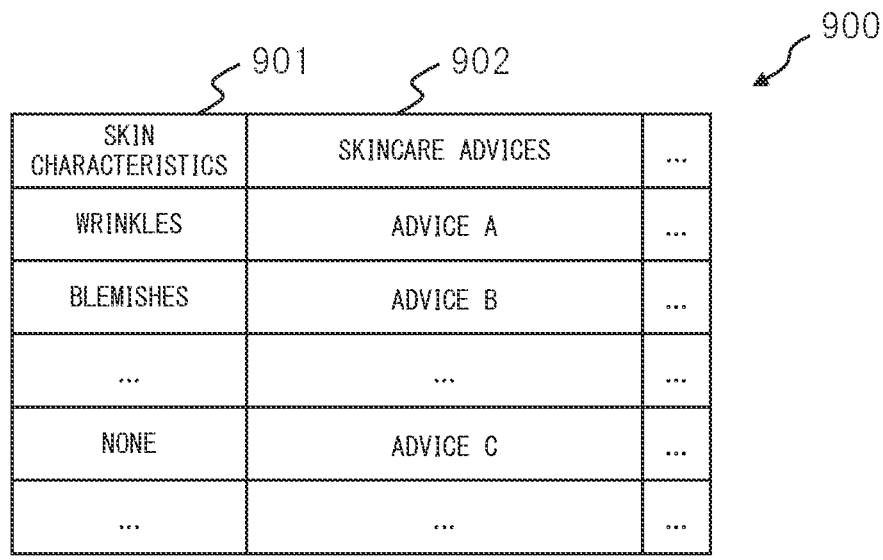
FIG. 9A shows an example of the data structure of a skincare advice table 900.

FIG. 9A shows an example of the data structure of the skincare advice table. The skincare advice table 900 stores skin characteristics 901 and skincare advices 902 in association with each other. In the skin characteristics 901, information for identifying items of certain skin characteristics is stored. In the skincare advices 902, information for identifying skincare advices is stored. In the skincare advices 902, text data representing skincare advices to be presented to users may be stored.

With reference to FIG. 3 again, the identifying unit 354 refers to the skincare advice table 900 to identify a skincare advice associated with the selected skin characteristic as a skincare advice to be proposed to the user. If none of the skin characteristics is selected, it identifies a skincare advice stored in association with skin characteristic "none" as a skincare advice to be proposed to the user. If multiple skin characteristics are selected, it may identify multiple skincare advices respectively associated with the skin characteristics or some of the skincare advices in preset priority order as skincare advices to be proposed to the user.

Figure 9B:
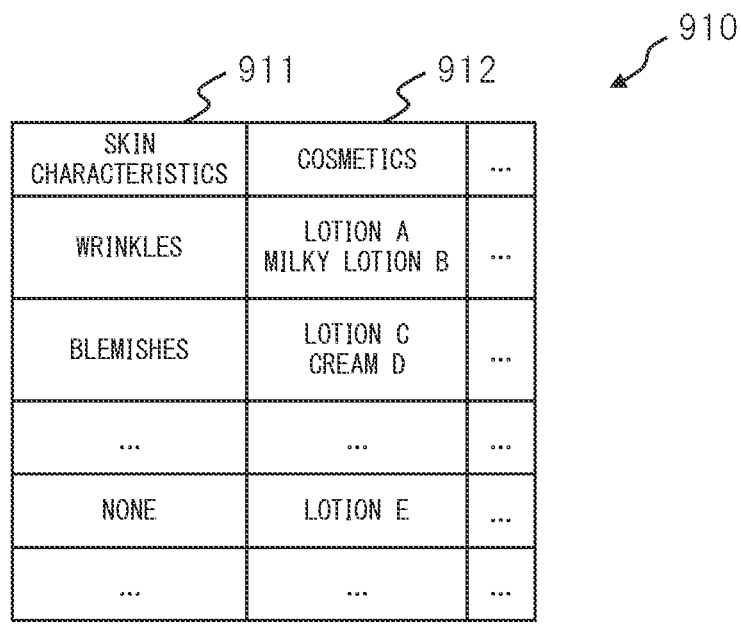
FIG. 9B shows an example of the data structure of a cosmetic table 910.

FIG. 9B shows an example of the data structure of the cosmetic table. The cosmetic table 910 stores skin characteristics 911 and cosmetics 912 in association with each other. In the skin characteristics 911, information for identifying items of certain skin characteristics is stored. In the cosmetics 912, information for identifying cosmetics is stored.

With reference to FIG. 3 again, the identifying unit 354 refers to the cosmetic table 910 to identify a cosmetic associated with the selected skin characteristic as a cosmetic to be proposed to the user. If none of the skin characteristics is selected, it identifies a cosmetic stored in association with skin characteristic "none" as a cosmetic to be proposed to the user. If multiple skin characteristics are selected, it may identify multiple cosmetics respectively associated with the skin characteristics or some of the cosmetics in preset priority order as cosmetics to be proposed to the user.

The identifying unit 354 may further identify information on skin stability to be presented to the user, based on the selected skin characteristic. The information on skin stability is, for example, information serving as a criterion for a user to keep the skin healthy, such as the user's tolerance to troubles related to the skin, or information on signs of troubles related to the skin. The information on skin stability may be information on a response to a stimulus to the skin or on a reaction to various ingredients contained in cosmetics.

In this way, the identifying unit 354 identifies a skincare advice and a cosmetic to be proposed to the user. The identifying unit 354 may identify only a skincare advice or a cosmetic.

The presenting unit 355 presents counseling information including information on the identified skincare advice and cosmetic to the user. For example, the presenting unit 355 generates display data for displaying, on the display unit 33, a counseling information display image for presenting the counseling information including information on a skincare advice and a cosmetic to the user. The presenting unit 355 supplies the generated display data to the display unit 33. In this way, the presenting unit 355 achieves presentation of counseling information to the user.

Figure 10:
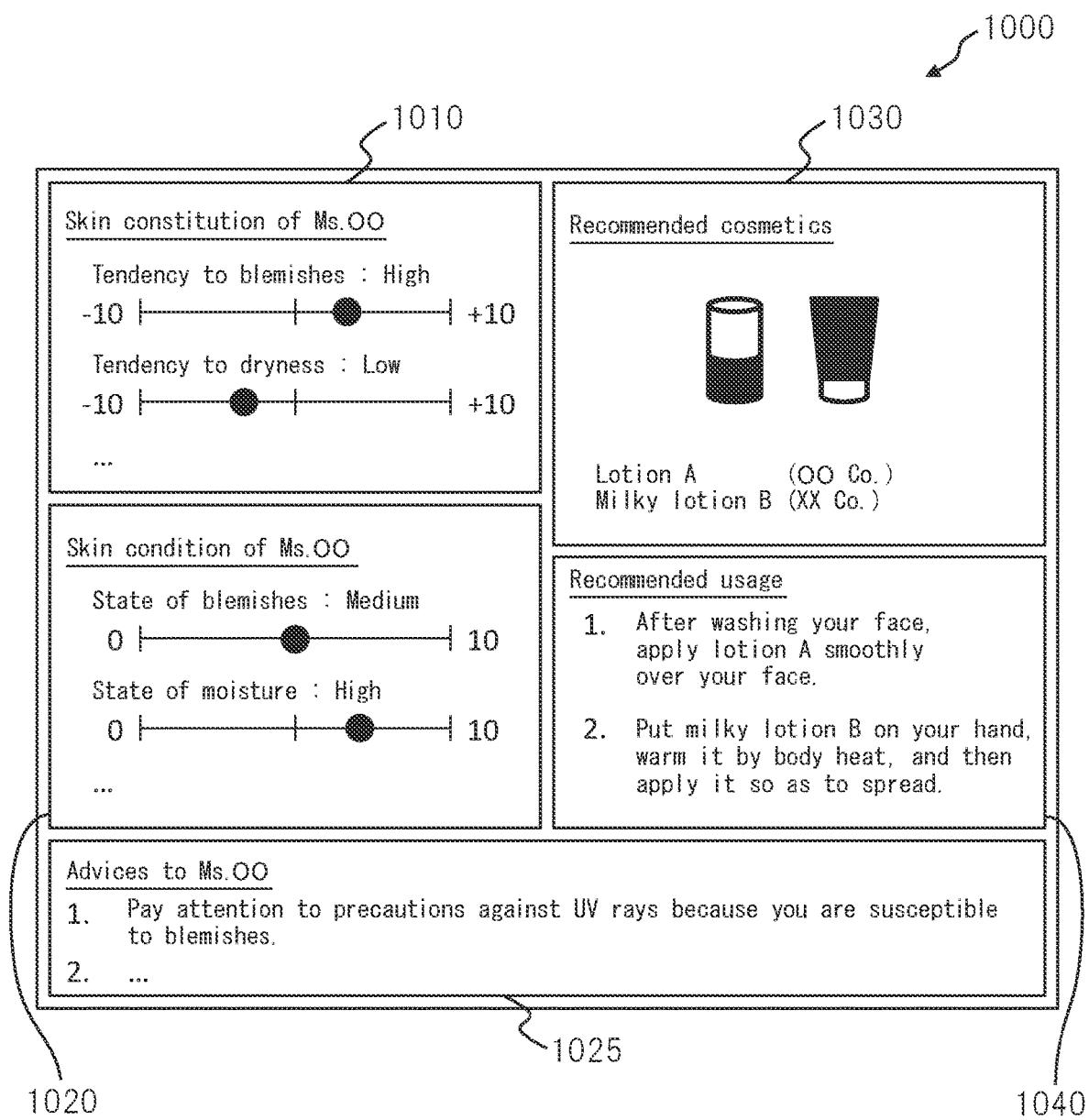
FIG. 10 shows an example of a counseling information display image 1000.

FIG. 10 shows an example of the counseling information display image. A counseling information display image 1000 includes an area 1010 displaying the result of a genetic test, an area 1020 displaying the result of a stratum corneum test, an area 1025 displaying skincare advices, an area 1030 displaying cosmetic information, and an area 1040 displaying usage information.

The area 1010 displays information including skin constitution. For example, the area 1010 displays information representing genetic characteristics for each skin characteristic. The area 1020 displays information including skin capability. For example, the area 1020 displays information representing the degree of external and internal risk for each skin characteristic. The area 1025 displays advices related to skincare that do not depend on the types of cosmetics, based on the genetic characteristics and the degree of external and internal risk of each skin characteristic. The area 1030 displays the names and images of the identified cosmetics. The area 1040 displays recommended usage of the identified cosmetics.

The counseling information presented by the presenting unit 355 may include information on the skin stability identified by the identifying unit 354. The counseling information presented by the presenting unit 355 may include only information on skincare advices or on cosmetics.

Figure 11:
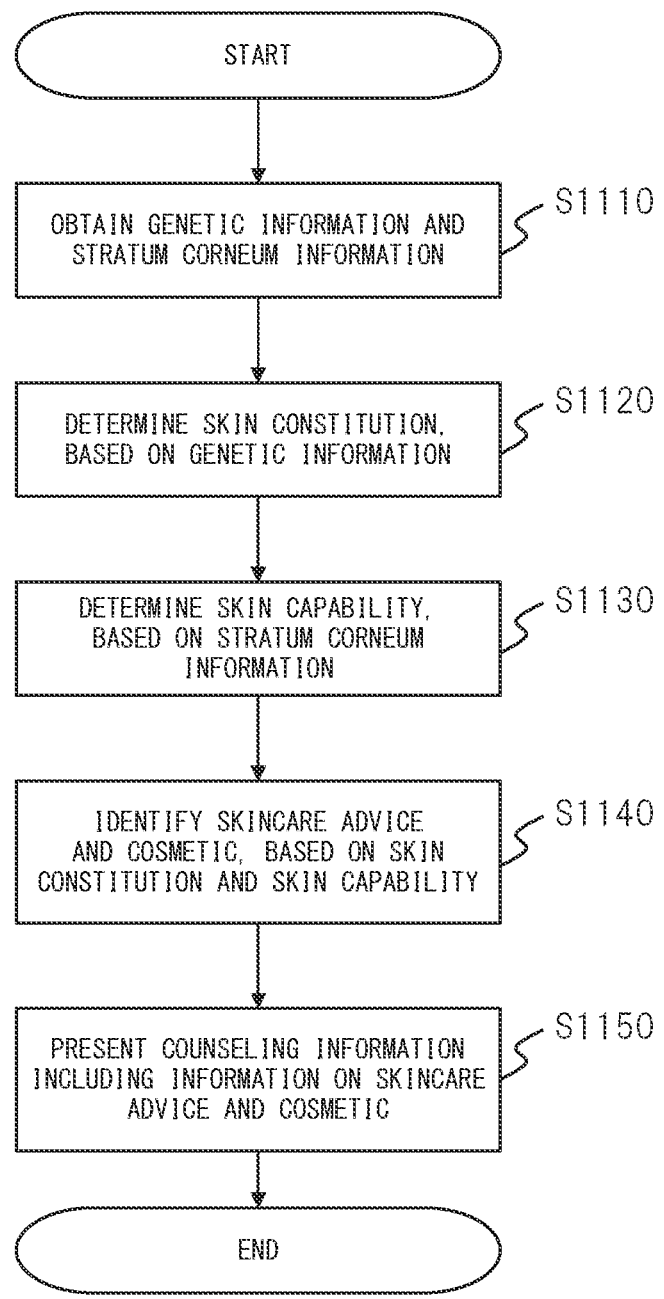
FIG. 11 is a flowchart showing an example of steps of processing by the counseling device 3.

FIG. 11 is a flowchart showing an example of steps of processing by the counseling device 3. First, the obtaining unit 351 obtains genetic information representing the result of a genetic test on a user and stratum corneum information representing the result of a stratum corneum test on the user (S1110). Then, the skin constitution determining unit 352 determines skin constitution of the user, based on the genetic information (S1120). Then, the skin capability determining unit 353 determines skin capability of the user, based on the stratum corneum information (S1130). Then, the identifying unit 354 identifies a skincare advice and a cosmetic to be proposed to the user, based on the skin constitution and the skin capability (S1140). Then, the presenting unit 355 presents counseling information including information on a skincare advice and a cosmetic to the user (S1150), and terminates a series of operations.

As described above, the counseling device 3 includes the obtaining unit 351 that obtains genetic information representing the result of a genetic test on a user and stratum corneum information representing the result of a stratum corneum test on the user; the skin constitution determining unit 352 that determines skin constitution of the user, based on the genetic information; the skin capability determining unit 353 that determines skin capability of the user, based on the stratum corneum information; the identifying unit 354 that identifies a skincare advice and a cosmetic to be proposed to the user, based on the skin constitution and the skin capability; and the presenting unit 355 that presents counseling information including information on the skincare advice and cosmetic to the user. Such features enable the counseling device 3 to present information on more appropriate cosmetics, taking account of genetic characteristics and external and internal risk factors. A user can be presented with information on cosmetics useful to the skin of the future, based on the genetic characteristics, and information on cosmetics useful to the skin of the present and the near future, based on the external and internal risk. This eliminates the need for the user to be presented with counseling information multiple times, and thus reduces the number of times of processing in the counseling device 3, reducing the processing load.

In the counseling device 3, counseling information includes information on the skin constitution and the skin capability. This enables the counseling device 3 to provide information on genetic characteristics and external and internal risk of the user's skin and to assist the user in choosing an appropriate skincare method and cosmetic by himself/herself.

In the counseling device 3, the skin constitution is information representing the degree of risk based on genetic characteristics of each skin characteristic, and the skin capability is information representing the degree of external and internal risk of each skin characteristic. The identifying unit 354 identifies a skincare advice and/or a cosmetic according to skin characteristics regarding which it is determined that genetic characteristics are high, from the skin constitution information, and that external and internal risk is high, from the skin capability information. Such features enable the counseling device 3 to present to the user a skincare advice and a cosmetic suitable for improving skin characteristics regarding which it is determined that both the risk based on genetic characteristics and the external and internal risk are high and thus prompt treatment is required.

The counseling device 3 is not limited to the above embodiment. The following describes other embodiments of the counseling device 3. The same reference numerals will be assigned to the same components, and explanation thereof will be omitted as appropriate.

Modified Example 1

In the above embodiment, the identifying unit 354 identifies a skincare advice and a cosmetic according to skin characteristics regarding which the skin constitution indicates that risk based on genetic characteristics is high and the skin capability indicates that external and internal risk is high. However, the invention is not limited thereto. The identifying unit 354 may identify a skin characteristic having high external and internal risk, based on the skin capability; a mechanism of deterioration of the skin characteristic, based on the skin constitution; and a skincare advice and/or a cosmetic, based on the identified skin characteristic and mechanism.

For example, the skin constitution determining unit 352 refers to an SNP table 600*a* stored in the storage unit 31 to determine the degree of genetic characteristics in the mechanism of deterioration of the skin characteristic, based on the genetic information.

FIG. 12 shows an example of the data structure of the SNP table 600a. The SNP table 600a stores RS numbers 610, skin characteristics 620, mechanisms 640, and effects 630 in association with each other. In the mechanisms 640, information for identifying mechanisms by which the associated skin characteristics change is stored. Multiple mechanisms may be associated with a single skin characteristic. This enables appropriately associating the skin characteristics with the mechanisms even if there are multiple mechanisms by which a skin characteristic changes.

In the example shown in FIG. 12, mutation type at RS number "rs1800629" is stored in association with skin characteristic "wrinkles," mechanism "inflammation," and effect "positive." This indicates that a user having the mutation type at SNP corresponding to RS number "rs1800629" is likely to have skin characteristic "wrinkles." This is because the mutation type at SNP corresponding to RS number "rs1800629" has the effect of "being likely to increase production of inflammatory factor TNF," and the effect of being likely to have skin characteristic "wrinkles." In other words, the SNP table 600a stores information indicating that a user having the mutation type at SNP corresponding to RS number "rs1800629" has a genetic predisposition to have more inflammation of skin and thus more wrinkles than a user who does not have this mutation type at SNP. Additionally, mutation type at RS number "rs1107946" is stored in association with skin characteristic "wrinkles," mechanism "production of type I collagen," and effect "negative." This indicates that a user having the mutation type at SNP corresponding to RS number "rs1107946" is unlikely to have skin characteristic "wrinkles." This is because the mutation type at SNP corresponding to RS number "rs1107946" is known to have the effect of "being likely to increase production of type I collagen," and deterioration of collagen of dermis affects skin characteristic "wrinkles." In other words, the SNP table 600a stores information indicating that a user having the mutation type at SNP corresponding to RS number "rs1107946" has a genetic predisposition to produce more type I collagen and thus have less wrinkles than a user who does not have this mutation type at SNP.

The skin constitution determining unit 352 selects a skin characteristic and a mechanism to compute a skin constitution score of. The skin constitution determining unit 352 refers to the SNP table 600a, and counts the number of RS numbers associated with the selected skin characteristic and mechanism and with effect "positive" of the mutation type at RS numbers included in the genetic information. The skin constitution determining unit 352 also counts the number of mutation type at RS numbers associated with the selected skin characteristic and mechanism and with effect "negative" of the mutation type at RS numbers included in the genetic information. Then, the skin constitution determining unit 352 subtracts the number of mutation type at RS numbers associated with effect "negative" from that of RS numbers associated with effect "positive" to compute a skin constitution score of the selected skin characteristic and mechanism.

The skin constitution determining unit 352 executes the above procedure for each skin characteristic and mechanism to compute a skin constitution score for each mechanism.

Additionally, the skin constitution determining unit 352 refers to a table 700a for determining genetic characteristics stored in the storage unit 31 to determine the degree of genetic characteristics for each mechanism, based on the skin constitution scores computed for each mechanism.

FIG. 13 shows an example of the data structure of the table 700a for determining genetic characteristics. The table 700a stores skin characteristics 710, mechanisms 740, risk criteria 720, risk decisions 730, and other data in association with each other. In the mechanism 740, information for identifying mechanisms is stored.

As shown in FIG. 13, if the skin constitution score of inflammation is "1 or 2," it is determined that risk based on genetic characteristics related to skin pigmented spots caused by inflammation is high. If the skin constitution score of inflammation is "0," it is determined that risk based on genetic characteristics related to skin pigmented spots are medium. If the skin constitution score of inflammation is "−2 or −1," it is determined that risk based on genetic characteristics related to skin pigmented spots are low.

The skin constitution determining unit 352 selects a mechanism regarding which the degree of genetic characteristics will be determined. The skin constitution determining unit 352 compares the risk criteria associated with the selected mechanism with the skin constitution score of the selected mechanism to determine the degree of genetic characteristics regarding the selected mechanism. The skin constitution determining unit 352 executes the above process for each mechanism to determine the degree of genetic characteristics for each mechanism, and thereby generates skin constitution information.

The identifying unit 354 identifies a cosmetic to be proposed to the user, based on the skin constitution information and the skin capability information. The identifying unit 354 selects a skin characteristic regarding which the skin capability indicates that external and internal risk is high. Of the mechanisms associated with the selected skin characteristic, the identifying unit 354 selects a mechanism regarding which the skin constitution indicates that risk based on genetic characteristics is high. The identifying unit 354 identifies a cosmetic corresponding to the selected mechanism as a cosmetic to be proposed to the user.

The above features enable the counseling device 3 to present a cosmetic to treat that change in a skin characteristic having high external and internal risk which is caused by a mechanism whose degree of genetic characteristics is high, of the mechanisms of deterioration of skin characteristics.

Modified Example 2

In the counseling device 3, the identifying unit 354 may identify a first cosmetic, based on the skin constitution, and a second cosmetic, based on the skin capability. For example, the identifying unit 354 identifies a first cosmetic, depending on a skin characteristic regarding which the skin constitution indicates that risk based on genetic characteristics is high. The identifying unit 354 also identifies a second cosmetic, depending on a skin characteristic regarding which the skin capability indicates that external and internal risk is high. The presenting unit 355 presents counseling information including information on the identified first and second cosmetics to the user. Such features enable the counseling device 3 to present cosmetics appropriate for the user's skin on a long-term basis in order to cope with problems that have arisen and may arise in the future in the user's skin.

Modified Example 3

In the counseling device 3, the obtaining unit 351 may obtain questionnaire information of the user, and the identifying unit 354 may identify a cosmetic to be presented to the user, further based on the questionnaire information.

For example, the obtaining unit 351 generates image data for displaying a questionnaire information input screen, and causes the display unit 33 to display the questionnaire information input screen. The obtaining unit 351 obtains information inputted into the displayed questionnaire information input screen by a user operating the operation unit 32, thereby obtaining the questionnaire information.

FIG. 14 shows an example of a questionnaire information input screen 1400. The questionnaire information input screen 1400 includes question areas 1410, answer areas 1420 respectively corresponding to the question areas, and a send button 1430. A user operates the operation unit 32 to input into the answer areas 1420 answers to questions displayed in the question areas 1410. After answering the questions, the user selects the send button 1430. In response to the selection of the send button 1430, the obtaining unit 351 obtains the answers inputted into the answer areas 1420 to obtain questionnaire information.

The questionnaire information may include attribute information of the user, such as gender, age, diet, the state of exposure to sunlight in everyday life, the length of sleep, bedtime and wake-up time, the degree of easiness of falling asleep, smoking or non-smoking, the presence or absence of experience of skin roughness, the degree of current stress, the menstrual cycle, and hours of sleep. The questionnaire information may include preference information related to the user's preference. The attribute information and the preference information may be obtained without the user answering questions. For example, the obtaining unit 351 presents multiple images in the question areas 1410 of the questionnaire information input screen 1400, and makes the user select an image, of the multiple images, matching his/her preference in the answer areas 1420, thereby obtaining the preference information of the user. The obtaining unit 351 may use a measuring device (not shown) to obtain information on the user's expression or electroencephalogram, and obtain the attribute information or preference information of the user, based on the obtained information. The obtaining unit 351 may obtain the attribute information or preference information of the user, based on the user's behavioral characteristics or mental changes.

Then, the identifying unit 354 identifies a cosmetic to be presented to the user, further based on the questionnaire information. For example, the identifying unit 354 selects a skin characteristic regarding which the skin constitution information indicates that risk based on genetic characteristics is high and the skin capability information indicates that external and internal risk is high. The identifying unit 354 refers to a skincare advice table 900a stored in the storage unit 31 to identify a skincare advice and a cosmetic corresponding to the selected skin characteristic and the questionnaire information as a skincare advice and a cosmetic to be proposed to the user.

Figure 15:
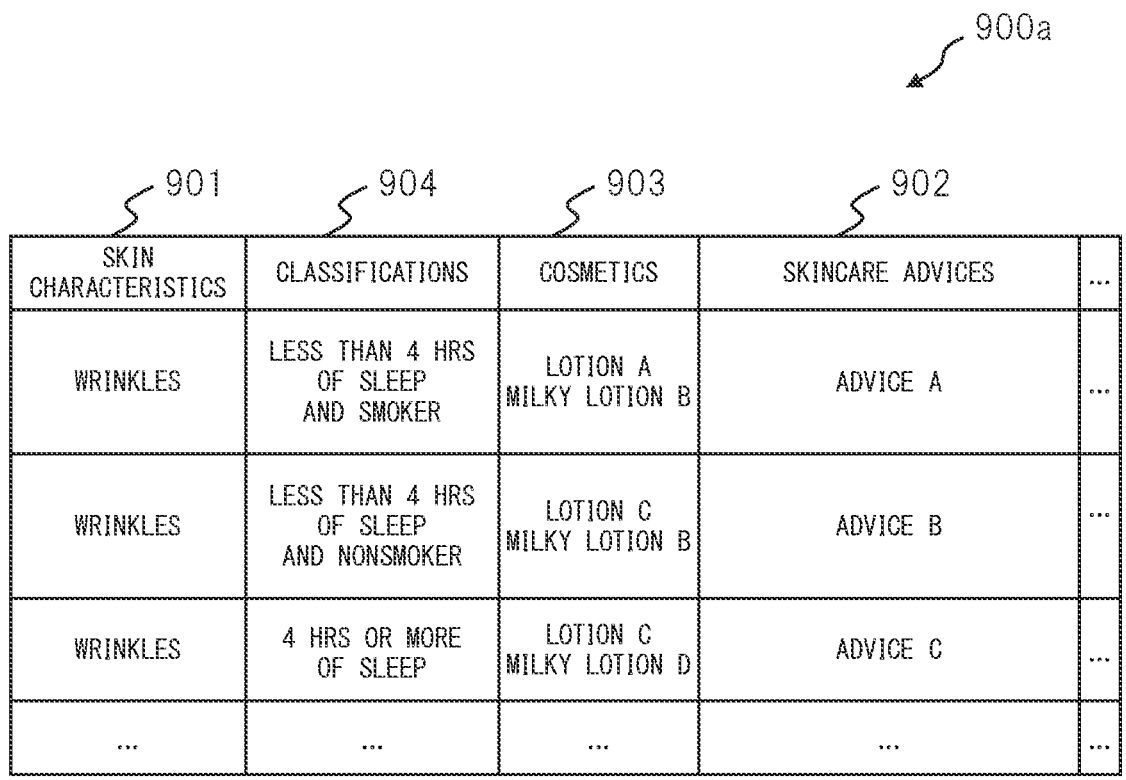

FIG. 15 shows an example of the data structure of the skincare advice table 900a. The skincare advice table 900a stores skin characteristics 901, classifications 904, cosmetics 903, and skincare advices 902 in association with each other. In the cosmetics 903, information for identifying cosmetics is stored. In the classifications 904, conditions for classifying users based on the questionnaire information obtained by the obtaining unit 351 are stored.

The identifying unit 354 refers to the skincare advice table 900a to identify a classification whose condition the questionnaire information obtained by the obtaining unit 351 satisfies, of the classifications associated with the selected skin characteristic. The identifying unit 354 identifies a skincare advice and/or a cosmetic associated with the identified classification as a skincare advice and/or a cosmetic to be proposed to the user.

The above features enable the counseling device 3 to present a skincare advice and/or a cosmetic matching the user's lifestyle, based on the questionnaire information of the user. Additionally, the counseling device 3 can present a skincare advice and/or a cosmetic matching the user's preference, based on the questionnaire information of the user, enabling raising the user's feeling of satisfaction.

Modified Example 4

In the counseling device 3, the stratum corneum information may include the results of stratum corneum tests obtained at different times, and the skin capability determining unit 353 may determine the changing pattern of skin capability, based on the stratum corneum information.

In this case, the obtaining unit 351 obtains stratum corneum information including the results of stratum corneum tests obtained at different times. The obtaining unit 351 receives information representing the result of a stratum corneum test from the stratum corneum test device 2 via the communication unit 34. The obtaining unit 351 stores the received information representing the result of a stratum corneum test in the storage unit 31, and obtains from the storage unit 31 information stored therein and representing the results of stratum corneum tests obtained at times different from the time of acquisition of the received result of a stratum corneum test. In this way, the obtaining unit 351 obtains stratum corneum information including the results of stratum corneum tests obtained at different times.

The skin capability determining unit 353 determines the changing pattern of skin capability, based on the stratum corneum information. For example, the skin capability determining unit 353 refers to a table 1600 for determining changing patterns stored in the storage unit 31 to determine skin capability representing the degree of external and internal risk for each skin characteristic and a changing pattern representing the trend of changes in the external and internal risk for each skin characteristic.

Figure 16:
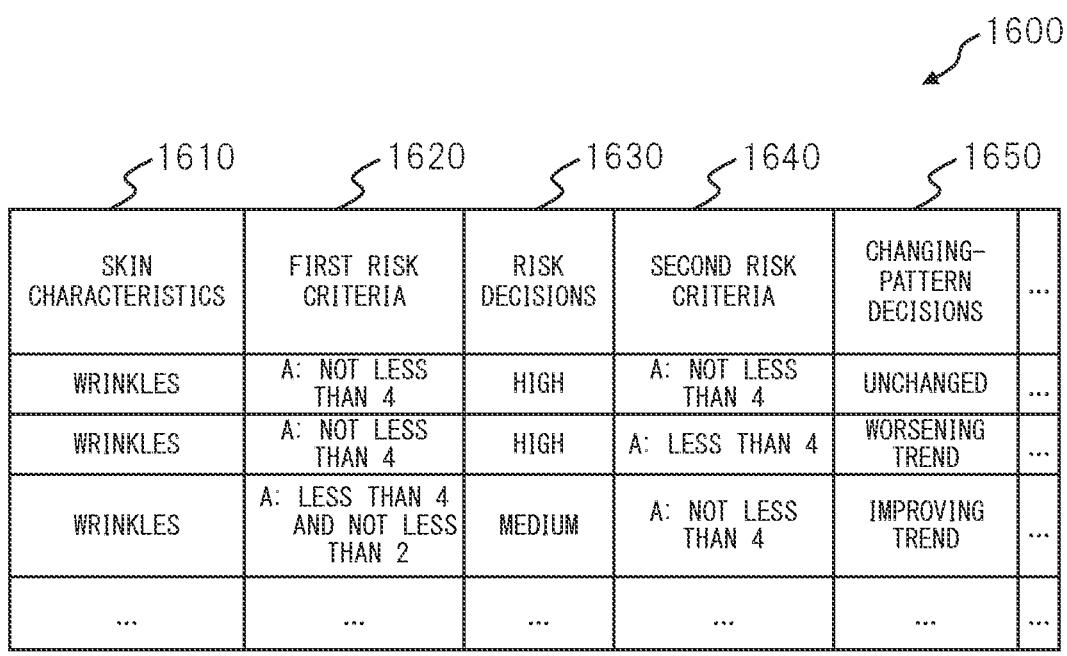
FIG. 16 shows an example of the data structure of a table 1600 for determining changing patterns.

FIG. 16 shows an example of the data structure of the table 1600 for determining changing patterns. The table 1600 stores skin characteristics 1610, first risk criteria 1620, risk decisions 1630, second risk criteria 1640, and changing-pattern decisions 1650 in association with each other. In the first risk criteria 1620, criteria related to the received result of a stratum corneum test (hereafter, "first stratum corneum information") are stored. In the risk decisions 1630, information representing the degrees of external and internal risk for the case that the first risk criteria stored in association therewith are satisfied is stored. The degrees of external and internal risk stored in the risk decisions 1630 are determined based on only the first stratum corneum information. In other words, the degree of external and internal risk is information reflecting the current skin capability. In the second risk criteria 1640, criteria related to the results of stratum corneum tests obtained prior to the first stratum corneum information (hereafter, "second stratum corneum information") are stored. In each changing-pattern decision 1650, information for identifying the state of changes of the degree of external and internal risk for the case that the first and second risk criteria stored in association therewith are satisfied is stored. In the changing-pattern decisions 1650, for example, information such as "improving trend," "worsening trend," or "unchanged" is stored. The states of changes stored in the changing-pattern decisions 1650 are determined based on not only the first stratum corneum information but also the second stratum corneum information. In other words, the state of changes is information reflecting the current and past skin capability.

The skin capability determining unit 353 selects a skin characteristic regarding which the degree of external and internal risk and the changing pattern of skin will be determined. The skin capability determining unit 353 compares the first risk criterion associated with the selected skin characteristic with the types and measured amounts of the stratum corneum components included in the first stratum corneum information to determine the degree of external and internal risk regarding the selected skin characteristic. The skin capability determining unit 353 compares the second risk criterion associated with the selected and determined external and internal risk with the types and measured amounts of the stratum corneum components included in the second stratum corneum information to determine the changing pattern of skin regarding the selected skin characteristic.

The skin capability determining unit 353 executes the above procedure for each skin characteristic to determine the degree of external and internal risk and the changing pattern for each skin characteristic.

The identifying unit 354 identifies a skincare advice and/or a cosmetic, based on the skin constitution information and the skin capability information. For example, the identifying unit 354 identifies a skin characteristic regarding which the skin constitution information indicates that risk based on genetic characteristics are high and the skin capability information indicates that external and internal risk is high and that the changing pattern is "worsening trend" or "unchanged." The identifying unit 354 identifies a skincare advice and a cosmetic according to the identified skin characteristic.

The above features enable the counseling device 3 to present a skincare advice and a cosmetic for treating a skin characteristic whose external and internal risk tends to increase prior to a skin characteristic whose external and internal risk tends to decrease, enabling presenting a skincare advice and a cosmetic more suitable for the user's skin.

Modified Example 5

In the counseling device 3, the obtaining unit 351 may obtain skin image information based on a skin image of the user's skin, and the identifying unit 354 may identify a skincare advice and a cosmetic, further based on the skin image information.

In this case, an image capturing device (not shown) communicably connected to the counseling device 3 via the network 4 captures the user's skin and generates a skin image of the user. The obtaining unit 351 obtains the user's skin image and the capturing time thereof from the image capturing device via the communication unit 34. The obtaining unit 351 applies a certain image analyzing algorithm to the obtained skin image to obtain skin image information. The skin image information is estimated information on the state of the surface or the interior of skin. The skin image information may be, for example, information representing the degree of risk for each skin characteristic, such as skin texture, wrinkles, moisture, pigmented spots, transparency, sebum, and brightness.

The identifying unit 354 identifies a skincare advice and/or a cosmetic, based on the skin constitution information, the skin capability information, and the skin image information. For example, the identifying unit 354 identifies a skin characteristic regarding which it is determined that genetic risk is high, based on the skin constitution information, that external and internal risk is high, based on the skin capability information, and that risk is high, based on the skin image information. The identifying unit 354 refers to the skincare advice table 900 and the cosmetic table 910 to identify a skincare advice and a cosmetic to be presented to the user, based on the identified skin characteristic.

Such use of a combination of the skin image information and the skin constitution information clarifies the difference between the intrinsic skin condition derived from the skin constitution information and the current skin condition derived from the skin image information. Additionally, the usefulness of the skincare advice and/or cosmetic becomes clearer, enabling the counseling device 3 to make a proposal persuasive to the user. The use of a combination of the skin image information and the skin constitution information also enables the counseling device 3 to propose precautions for a skin characteristic, for example, regarding which it is determined that risk is low, based on the skin image information, and that risk is high, based on the skin constitution information.

Modified Example 6

In the counseling device 3, the obtaining unit 351 may further obtain attribute information or preference information of the user and skin image information based on a skin image of the user's skin. Then, the identifying unit 354 may extract a factor affecting the user's skin, based on the skin capability, the attribute information or preference information, and the skin image information, and identify a skincare advice and a cosmetic, based on the skin constitution and the extracted factor.

The factor affecting the skin may be extracted from the attribute information or preference information. For example, if it is determined that external and internal risk related to "sunburn damage" of skin is high, based on the skin capability or the skin image information, the identifying unit 354 extracts information on "sunburn damage" (e.g., whether precautions against ultraviolet rays are sufficient) from the attribute information or preference information as a factor affecting the skin. The identifying unit 354 identifies a skincare advice and a cosmetic, based on the extracted factor and the skin constitution. For example, the identifying unit 354 identifies different skincare advices and cosmetics, depending on whether the user's precautions against ultraviolet rays are sufficient and whether the SNP score related to sunburn damage of the skin constitution of the user is not less than a certain value.

In this way, the user can be presented with a skincare advice, based on a factor included in the attribute information or preference information and supposed to greatly affect the user's skin. Since the attribute information or preference information is inputted by a user, based on self-awareness, a skincare advice based on the attribute information or preference information will be more persuasive for the user, increasing the possibility of the advice being put into practice. Additionally, since the attribute information or preference information greatly differs depending on users' lifestyle, more personalized skincare advices can be presented to each user.

As a factor affecting the skin, the identifying unit 354 may extract, for example, diet balance; intake of particular nutrients, such as vitamins and minerals; bedtime; hours of sleep; the state of exposure to ultraviolet rays and air pollution; and the degree of mental stress.

Modified Example 7

In the above description, the identifying unit 354 of the counseling device 3 identifies a skin characteristic, based on the skin constitution information and the skin capability information, and identifies a skincare advice and a cosmetic, based on the identified skin characteristic. However, the invention is not limited thereto. The identifying unit 354 may identify a skincare advice and/or a cosmetic, based on the genetic information, instead of the skin constitution information.

In this case, for example, the identifying unit 354 identifies a skin characteristic regarding which it is determined that external and internal risk is high, based on the skin capability information. The identifying unit 354 refers to the SNP table 600 to obtain the RS numbers of the SNPs associated with the identified skin characteristic. The identifying unit 354 determines whether the mutation type at SNPs respectively corresponding to the obtained RS numbers are included in the user's genes, based on the genetic information. The identifying unit 354 identifies a skincare advice and a cosmetic, based on the combination of the results of determination whether the mutation types at SNPs are included in the user's genes. The correspondence between combinations of the results of determination whether the mutation type at SNPs are included in the user's genes and skincare advices and cosmetics may be prestored in the storage unit 31.

In this way, the counseling device 3 can present a skincare advice and/or a cosmetic to the user, depending on a combination of SNPs. In other words, even if the skin constitution score is the same, the counseling device 3 can make different proposals, depending on combinations of SNPs, and thus can give advices matching the user's physical constitution well.

In the above description, the genetic information is used instead of the skin constitution information. However, the identifying unit 354 may identify a skincare advice and/or a cosmetic, based on the stratum corneum information, instead of the skin capability information.

Modified Example 8

In the counseling device 3, counseling information presented by the presenting unit 355 may include information on a community for the user to exchange information with another user having skin constitution similar to the user's or to obtain information on a skincare advice and a cosmetic.

In this case, the storage unit 31 further stores a user information table for managing information on users.

FIG. 17 shows an example of the data structure of a user information table 1700. The user information table 1700 stores identification information 1710, contact information 1720, genetic information 1730, groups 1740, and URLs 1750 in association with each other.

In the identification information 1710, information by which users are uniquely identifiable is stored. In the contact information 1720, information for presenting counseling information to the users is stored. In the contact information 1720, for example, the users' email addresses are stored. In the genetic information 1730, part or all of the users' genetic information obtained by the obtaining unit 351 is stored. In the genetic information 1730 of the example shown in FIG. 17, information on associations between RS numbers of SNPs and information indicating whether the users have the SNPs corresponding to the respective RS numbers are stored. In the groups 1740, information for identifying groups of skin constitution to which the users belong is stored; this grouping is based on the genetic information 1730 of the users. Each user can receive information dispatched to the group to which the user belongs via a community site, and also dispatch information to the group via the community site. In the URLs 1750, URLs for the users to log in to community sites are stored. The URLs may be character strings including login information for the users to log in to the community sites and differing among the users. If different community sites are provided for the respective groups, the URLs may be character strings differing among the groups to which the users belong. Each URL is an example of information on a community.

In addition to the genetic information and the stratum corneum information, the obtaining unit 351 further obtains contact information for sending information on a community to the users' communication terminals. The obtaining unit 351 may obtain the contact information by making the users input the contact information via the operation unit 32 or from the users' communication terminals via the communication unit 34. The obtaining unit 351 stores the contact information and the genetic information in the user information table 1700.

In addition to identifying a skincare advice and/or a cosmetic to be presented to a user, the identifying unit 354 further identifies the group to which the user belongs, based on the genetic information 1730 of the user information table 1700. For example, the identifying unit 354 identifies the group to which the user belongs according to the combination of the RS numbers of SNPs in the genetic information 1730 and the information indicating whether the mutation types at SNPs corresponding to the respective RS numbers are included. The group may be identified, for example, based on the combination of the RS numbers and the information that are prestored in the storage unit 31; this information indicates whether the SNPs corresponding to the RS numbers are included. Upon identifying the group to which the user belongs, the identifying unit 354 stores the identified group in the user information table 1700. This results in users having similar skin constitution belonging to the same group.

The identifying unit 354 further identifies the URL for the user to log in to a community site, based on the group to which the user belongs. For example, of the URLs respectively corresponding to the groups prestored in the storage unit 31, the identifying unit 354 selects the URL corresponding to the group to which the user belongs, thereby identifying the URL.

The presenting unit 355 generates display data for displaying, on the user's communication terminal, a counseling information display image 1000*a* for presenting, to the user, counseling information including information on the skincare advice and cosmetic and the URL identified by the identifying unit 354.

Figure 18:
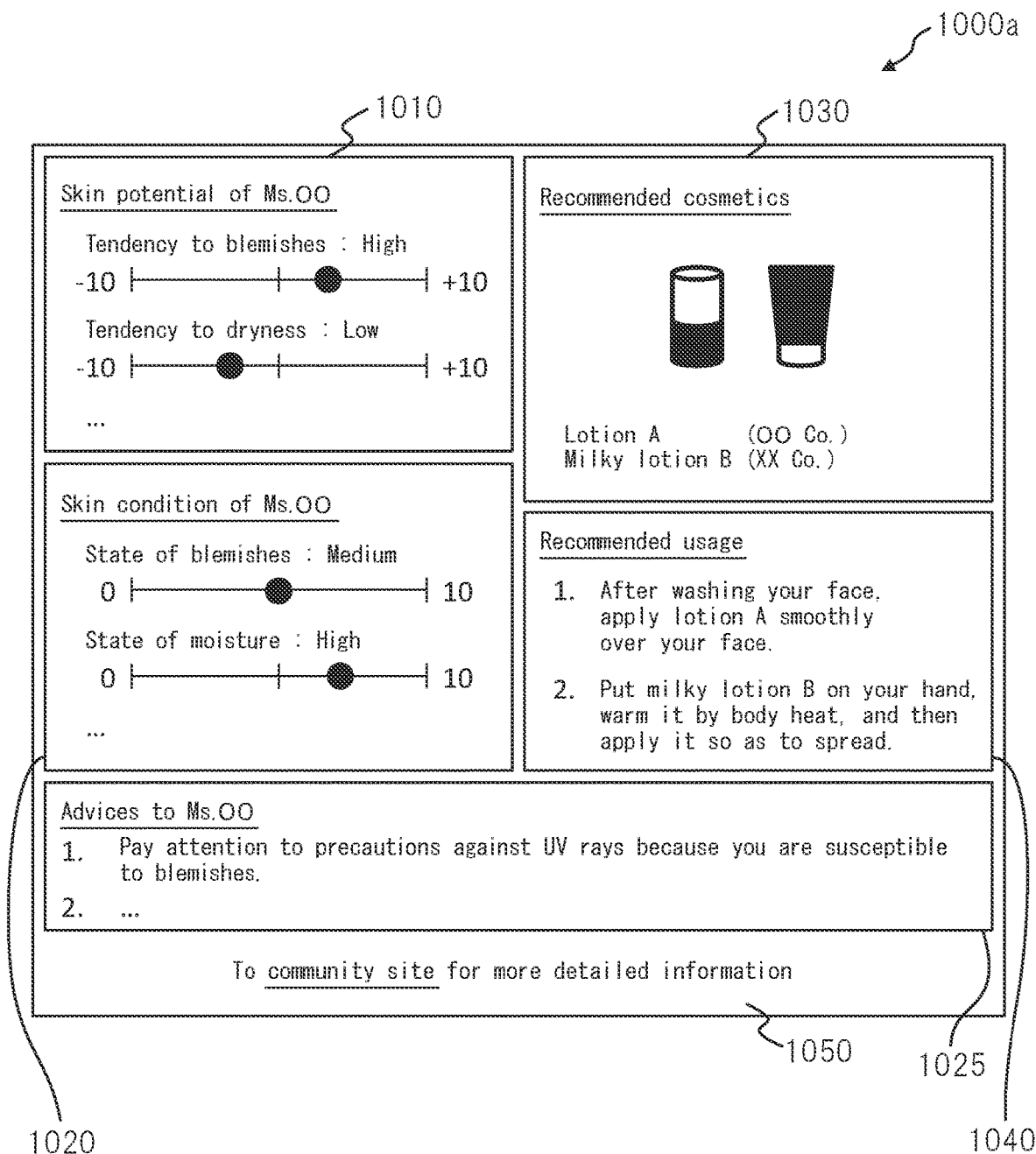

FIG. 18 shows an example of the counseling information display image 1000*a*. The counseling information display image 1000*a* includes an area 1010 displaying the result of a genetic test, an area 1020 displaying the result of a stratum corneum test, an area 1025 displaying skincare advices, an area 1030 displaying cosmetic information, an area 1040 displaying usage information, and an area 1050 displaying text. The area 1050 displays a character string for guiding the user to a community site. In the example shown in FIG.

18, the character string displayed in the area 1050 includes a hyperlink to the URL identified by the identifying unit 354. The area 1050 may display the URL identified by the identifying unit 354 in the form of a character string.

The presenting unit 355 refers to the user information table 1700 in the storage unit 31 to obtain the contact information of the user. Then, the presenting unit 355 sends the display data of the counseling information display image to the user's communication terminal, based on the obtained contact information. In this way, the presenting unit 355 presents counseling information including information on a community to the user.

In this way, the counseling device 3 can provide a community where a user exchanges information with another user having skin constitution similar to the user's. The counseling device 3 dispatches information matching the skin constitution of the users at the community, enabling continuously presenting information on skincare advices and cosmetics more appropriate to the users.

In the above description, the presenting unit 355 sends the display data of the counseling information display image 1000*a* to present counseling information to the user. However, the invention is not limited thereto, and the information may be presented by various methods. For example, the presenting unit 355 may present a counseling information display image to users in the form of a web page.

The presenting unit 355 may send only the URL of a community site to the user. In this case, the community site may be configured so as to present a counseling information display image to the user.

As above, preferable embodiments of the present invention have been described, but the present invention is not limited to these embodiments. Note that those skilled in the art can apply various changes, substitutions, and modifications thereto without departing from the idea and scope of the present invention.

REFERENCE SIGNS LIST

S counseling system
1 genetic test device
2 stratum corneum test device
3 counseling device
31 storage unit
32 operation unit
33 display unit
34 communication unit
35 processing unit
351 obtaining unit
352 skin constitution determining unit
353 skin capability determining unit
354 identifying unit
355 presenting unit

The invention claimed is:

1. A skincare advice method of a counseling device having an obtaining unit, a skin constitution determining unit, a skin capability determining unit, an identifying unit, and a presenting unit, the method comprising:
   performing a genetic test on a user and a stratum corneum test on the user by the obtaining unit, to obtain stratum corneum information including an amount of at least one of SCCA-1, MMP-9, IL-1ra, and IL-1alpha;
   determining skin constitution of the user, based on the genetic information by the skin characteristic determining unit;
   determining skin capability of the user, based on the stratum corneum information by the skin capability determining unit;
   identifying a skincare advice and/or cosmetic to be proposed to the user, based on the skin constitution and the skin capability by the identifying unit; and
   presenting counseling information including information on the identified skincare advice and/or cosmetic to the user by displaying a counseling information display image including the counseling information on a display device by the presenting unit.

2. The skincare advice method according to claim 1, wherein the counseling information includes information on the skin constitution and information on the skin capability.

3. The skincare advice method according to claim 1, further comprising
   obtaining attribute information or preference information of the user, wherein
   identifying the skincare advice and/or cosmetic is further based on the attribute information or preference information.

4. The skincare advice method according to claim 1, wherein the stratum corneum information includes results of stratum corneum tests obtained at different time, and determining the skin capability comprises determining a changing pattern of skin capability on the basis of the stratum corneum information.

5. The skincare advice method according to claim 1, further comprising
   obtaining skin image information based on a skin image of the user's skin, wherein
   identifying the skincare advice and/or cosmetic is further based on the skin image information.

6. The skincare advice method according to claim 1, further comprising
   obtaining attribute information or preference information of the user and skin image information based on a skin image of the user's skin, wherein
   identifying the skincare advice and/or cosmetic comprises
   extracting a factor affecting the user's skin, based on the skin capability, the attribute information or preference information, and the skin image information, and
   identifying the skincare advice and/or cosmetic, based on the skin constitution and the extracted factor.

7. The skincare advice method according to claim 1, wherein the counseling information includes information on a community for a user to exchange information with another user or to obtain information on a skincare advice and/or a cosmetic.

8. The skincare advice method according to claim 1, wherein the counseling information includes information on skin stability.

9. A counseling device for skincare advice comprising a processor, wherein the processor is configured to:
   perform a genetic test on a user to obtain genetic information and a stratum corneum test on the user to obtain stratum corneum information including an amount of at least one of SCCA-1, MMP-9, IL-1ra, and IL-1 alpha;
   determine skin constitution of the user, based on the genetic information;
   determine skin capability of the user, based on the stratum corneum information;
   identify a skincare advice and/or a cosmetic to be proposed to the user, based on the skin constitution and the skin capability; and
   present counseling information including information on the identified skincare advice and/or cosmetic to the user by displaying a counseling information display image including the counseling information on a display device.

10. The skincare advice method according to claim 1, wherein the genetic information includes presence or absence of plurality of SNPs related to a plurality of skin characteristics.

11. The skincare advice method according to claim 10, wherein the skin constitution of the user is determined by calculating skin constitution score for each of the plurality of skin characteristics based on the presence or absence of the SNPs related to each of the plurality of skin characteristics.

12. The counseling device according to claim 9, wherein the genetic information includes presence or absence of a plurality of SNPs related to a plurality of skin characteristics.

13. The counseling device according to claim 12, wherein the skin constitution determining unit determines the skin constitution of the user by calculating skin constitution score for each of the plurality of skin characteristics based on the presence or absence of the SNPs related to each of the plurality of skin characteristics.

14. A counseling device for skincare advice comprising one or more processors, wherein at least one of the processors is configured to:
perform a genetic test on a user to obtain genetic information and a stratum corneum test on the user to obtain stratum corneum information, the genetic information including presence or absence of a plurality of SNPs related to a skin characteristic, and the stratum corneum information including an amount of at least one of SCCA-1, MMP-1, IL-1ra, and IL-1alpha;
determine skin constitution of the user by computing an SNP score of a skin characteristic by counting SNPs with a positive effect on the skin characteristic and SNPs with a negative effect on the skin characteristic included in the genetic information;
determine skin capability of the user, based on the amount of at least one of SCCA-1, MMP-9, IL-1ra, and IL-1alpha included in the stratum corneum information;
identify a skincare advice and/or a cosmetic to be proposed to the user, based on the skin constitution and the skin capability; and
present counseling information including information on the identified skincare advice and/or cosmetic to the user by displaying a counseling information display image including the counseling information on a display device.

15. The skincare advice method of claim 1, wherein performing a genetic test comprises: (a) obtaining a genetic test specimen from the user's body; (b) purifying a nucleic acid from the genetic test specimen; and (c) generating a genetic test result regarding the purified nucleic acid, wherein the genetic test result comprises a presence or absence of one or more SNPs related to one or more skin characteristics.

16. The skincare advice method of claim 1, wherein identifying the skincare advice and/or a cosmetic to be proposed to the user is based on a combination of a genetic risk determined by the skin characteristic determining unit and an internal and external risk determined by the skin capability determining unit.

17. The counseling device according to claim 9, wherein identifying the skincare advice and/or a cosmetic to be proposed to the user is based on a combination of a genetic risk determined by the skin characteristic determining unit and an internal and external risk determined by the skin capability determining unit.

* * * * *